(12) United States Patent
Komurata et al.

(10) Patent No.: US 11,883,102 B2
(45) Date of Patent: Jan. 30, 2024

(54) VISUAL FUNCTION DETECTION APPARATUS, METHOD OF DETECTING VISUAL FUNCTION, AND PROGRAM

(71) Applicant: JVCKENWOOD Corporation, Yokohama (JP)

(72) Inventors: Miku Komurata, Yokohama (JP); Shuji Hakoshima, Yokohama (JP)

(73) Assignee: JVCKENWOOD Corporation, Yokohama (JP)

( * ) Notice: Subject to any disclaimer, the term of this patent is extended or adjusted under 35 U.S.C. 154(b) by 795 days.

(21) Appl. No.: 16/997,988

(22) Filed: Aug. 20, 2020

(65) Prior Publication Data

US 2020/0375454 A1 Dec. 3, 2020

Related U.S. Application Data

(63) Continuation of application No. PCT/JP2019/005155, filed on Feb. 13, 2019.

(30) Foreign Application Priority Data

Mar. 1, 2018 (JP) .................. 2018-036570

(51) Int. Cl.
*A61B 3/113* (2006.01)
*A61B 3/00* (2006.01)
*G06F 3/01* (2006.01)

(52) U.S. Cl.
CPC ............ *A61B 3/113* (2013.01); *A61B 3/0041* (2013.01); *G06F 3/013* (2013.01); *G06F 3/017* (2013.01)

(58) Field of Classification Search
CPC ......... A61B 3/113; A61B 3/0041; A61B 3/02; G06F 3/013; G06F 3/017

(Continued)

(56) References Cited

U.S. PATENT DOCUMENTS

2016/0363994 A1* 12/2016 Yokoya .................. G06F 3/013
2018/0020910 A1* 1/2018 Maeda ................... A61B 3/028
351/223

(Continued)

FOREIGN PATENT DOCUMENTS

JP 11-225964 8/1999
JP 2007-143665 6/2007

(Continued)

OTHER PUBLICATIONS

International Search Report and Written Opinion for International Application No. PCT/JP2019/005155 dated Apr. 2, 2019, 8 pages.

(Continued)

*Primary Examiner* — Mohammed A Hasan
(74) *Attorney, Agent, or Firm* — Amin, Turocy & Watson, LLP

(57) ABSTRACT

A visual function detection apparatus includes: a display controller configured to cause an image for determination to be displayed in a display region on a display screen of a display unit and move the image for determination within the display region; a gazing point detector configured to detect a position of a gazing point of a test subject observing the display screen; a relation detector configured to detect relation information among a position of the image for determination on the display screen, a moving direction of the image for determination, and a moving direction of the gazing point; and a visual function detector configured to detect a visual function of the test subject based on the relation information.

3 Claims, 16 Drawing Sheets

(58) Field of Classification Search
USPC .......................................................... 351/205
See application file for complete search history.

(56) References Cited

U.S. PATENT DOCUMENTS

2019/0317596 A1* 10/2019 Sato .................... G06F 3/04842
2020/0192091 A1*  6/2020 Huh ........................ G06T 11/60

FOREIGN PATENT DOCUMENTS

| JP | 4683280 | 5/2011 |
| JP | 2018-019978 | 2/2018 |
| WO | 2018/026858 | 2/2018 |

OTHER PUBLICATIONS

Morita, "Visual Acuity Measurement by Optokinetic Nystagmus Suppression Using Varied Contrasts: Macular Diseases and Functional Amblyopia", Journal of the eye, 2006, vol. 23, No. 12, pp. 1628-1630.
Written Opinion for International Application No. PCT/JP2019/005155 dated Apr. 2, 2019, 3 pages.

* cited by examiner

VISUAL FUNCTION DETECTION APPARATUS, METHOD OF DETECTING VISUAL FUNCTION, AND PROGRAM

CROSS-REFERENCE TO RELATED APPLICATIONS

This application is a Continuation of International Patent Application No. PCT/2019/005155 filed on Feb. 13, 2019, which claims the benefit of priority from Japanese Patent Application No. 2018-036570 filed on Mar. 1, 2018, the entire contents of both of which are incorporated herein by reference.

BACKGROUND

1. Technical Field

The present invention relates to a visual function detection apparatus, a method of detecting a visual function, and a program.

2. Description of the Related Art

Conventionally, there have been methods using Landolt rings for eyesight examinations. Japanese Laid-open Patent Publication No. 2007-143665 (JP-A-2007-143665) discloses a method of displaying Landolt rings on a screen to perform an eyesight examination, for example. Patent Literature 2 discloses a method of displaying an image with a striped pattern on a screen and causing an examiner to determine whether a test subject is seeing the image to perform an eyesight examination, for example.

However, in the method of displaying Landolt rings as in JP-A-2007-143665, the test subject is required to self-declare how he/she sees, and an appropriate examination may not be able to be performed depending on the test subject such as an infant. In the case of determining whether the test subject is seeing the image as described in Patent Literature 2, objective determination about whether the test subject is actually seeing the image is difficult. Thus, a technique capable of appropriately examining a visual function of the test subject is demanded.

In view of the above problems, an object of the present invention is to provide a visual function detection apparatus, a method of detecting a visual function, and a program capable of appropriately examining the visual function of the test subject.

SUMMARY

According to an aspect, a vision function detection apparatus includes: a display controller configured to cause an image for determination to be displayed in a display region on a display screen of a display unit, and move the image for determination within the display region; a gazing point detector configured to detect a position of a gazing point of a test subject observing the display screen; a relation detector configured to detect relation information between a moving direction of the image for determination and a moving direction of the gazing point; and a visual function detector configured to detect a visual function of the test subject based on the relation information.

According to another aspect, a vision function detection apparatus includes: a display controller configured to cause an image for determination to be displayed in a display region on a display screen of a display unit, and move the image for determination within the display region; a detector configured to detect movement of an eyeball of a test subject observing the display screen; a relation detector configured to detect relation information between a moving direction of the image for determination and a direction in which the eyeball moves; and a visual function detector configured to detect a visual function of the test subject based on the relation information.

According to another aspect, a method of detecting a vision function includes: performing display control to cause an image for determination to be displayed in a display region on a display screen of a display unit and moving the image for determination within the display region; performing gazing point detection to detect a position of a gazing point of a test subject observing the display screen; performing relation information detection to detect relation information between a moving direction of the image for determination and a moving direction of the gazing point; and performing visual function detection to detect a visual function of the test subject based on the relation information.

According to another aspect, a method of detecting a vision function includes: performing display control to cause an image for determination to be displayed in a display region on a display screen of a display unit and moving the image for determination within the display region; detecting movement of an eyeball of a test subject observing the display screen; performing relation information detection to detect relation information between a moving direction of the image for determination and a direction in which the eyeball moves; and performing visual function detection to detect a visual function of the test subject based on the relation information.

According to another aspect, a non-transitory computer-readable storage medium storing a program causes a computer to execute a method that includes: performing display control to cause an image for determination to be displayed in a display region on a display screen of a display unit and moving the image for determination within the display region; detecting movement of an eyeball of a test subject observing the display screen; performing relation information detection to detect relation information between a moving direction of the image for determination and a direction in which the eyeball moves; and performing visual function detection to detect a visual function of the test subject based on the relation information.

According to an aspect, a non-transitory computer-readable storage medium storing a program causes a computer to execute a method that includes: performing display control to cause an image for determination to be displayed in a display region on a display screen of a display unit and moving the image for determination within the display region; detecting movement of an eyeball of a test subject observing the display screen; performing relation information detection to detect relation information between a moving direction of the image for determination and a direction in which the eyeball moves; and performing visual function detection to detect a visual function of the test subject based on the relation information.

DETAILED DESCRIPTION

The following describes embodiments of a visual function detection apparatus, a method of detecting a visual function, and a program according to the present invention based on the accompanying drawings. These embodiments do not limit this invention. Components in the following embodiments include ones that can be replaced by those skilled in the art and are easy or substantially the same ones.

In the following description, positional relations among parts will be described by setting a three-dimensional global coordinate system. A direction parallel to a first axis on a certain plane is defined as an X-axial direction, a direction parallel to a second direction on the certain plane orthogonal to the first axis is defined as a Y-axial direction, and a direction parallel to a third axis orthogonal to each of the first axis and the second axis is defined as a Z-axial direction. The certain plane includes an XY plane.

(Visual Function Detection Apparatus)

Figure 1:
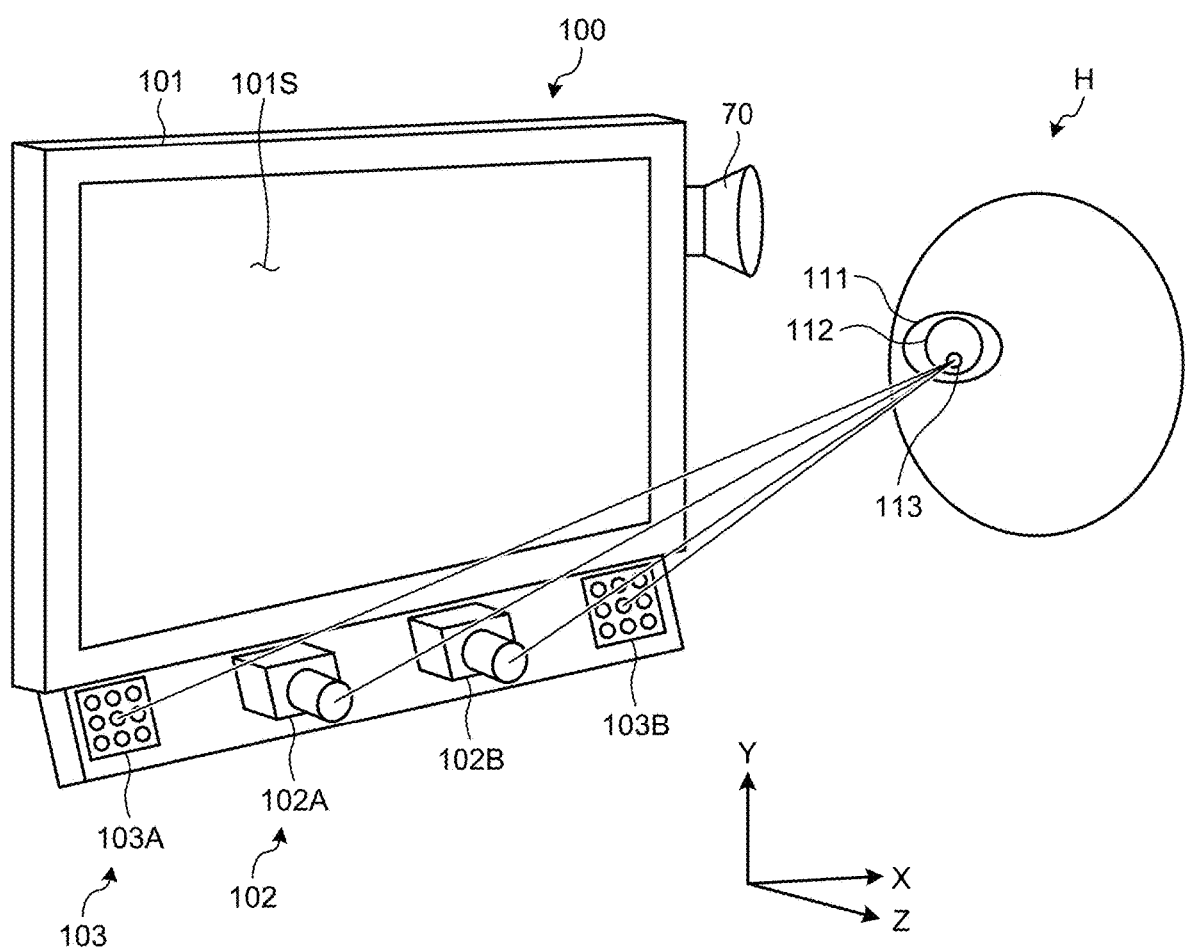
FIG. 1 is a perspective view schematically illustrating an example of a visual function detection apparatus according to an embodiment.

FIG. 1 is a schematic perspective view of an exemplary visual function detection apparatus according to the present embodiment. The visual function detection apparatus 100 is also used as an evaluation apparatus evaluating a test subject H. As illustrated in FIG. 1, the visual function detection apparatus 100 includes a display apparatus 101, a stereo camera apparatus 102, and an illumination apparatus 103.

The display apparatus 101 as a display unit includes a flat panel display such as a liquid crystal display (LCD) or an organic electroluminescence display (OLED). In the present embodiment, the display apparatus 101 has a display screen 101S. The display screen 101S displays images. The display screen 101S is substantially parallel to the XY plane. The X-axial direction is a right-and-left direction of the display screen 101S, the Y-axial direction is an up-and-down direction of the display screen 101S, and the Z-axial direction is a depth direction orthogonal to the display screen 101S.

The stereo camera apparatus 102 has a first camera 102A and a second camera 102B. The stereo camera apparatus 102 is placed below the display screen 101S of the display apparatus 101. The first camera 102A and the second camera 102B are placed in the X-axial direction. The first camera 102A is placed in a −X direction of the second camera 102B. The first camera 102A and the second camera 102B each include an infrared camera and have an optical system allowing near-infrared light with a wavelength of 850 [nm], for example, to pass and an imaging element that can receive the near-infrared light.

The illumination apparatus 103 has a first light source 103A and a second light source 103B. The illumination apparatus 103 is placed below the display screen 101S of the display apparatus 101. The first light source 103A and the second light source 103B are placed in the X-axial direction. The first light source 103A is placed in a −X direction of the first camera 102A. The second light source 103B is placed in a +X direction of the second camera 102B. The first light source 103A and the second light source 103B each include a light emitting diode (LED) light source and can each emit near-infrared light with a wavelength of 850 [nm], for example. The first light source 103A and the second light source 103B may be placed between the first camera 102A and the second camera 102B.

The illumination apparatus 103 emits near-infrared light as detection light to illuminate an eyeball 111 of the test subject H. The stereo camera apparatus 102 photographs the eyeball 111 with the second camera 102B when the eyeball 111 is irradiated with detection light emitted from the first light source 103A and photographs the eyeball 111 with the first camera 102A when the eyeball 111 is irradiated with detection light emitted from the second light source 103B.

A frame synchronization signal is output from at least either the first camera 102A or the second camera 102B. The first light source 103A and the second light source 103B emit the detection light based on the frame synchronization signal. The first camera 102A acquires image data of the eyeball 111 when the eyeball 111 is irradiated with the detection light emitted from the second light source 103B. The second camera 102B acquires image data of the eyeball 111 when the eyeball 111 is irradiated with the detection light emitted from the first light source 103A.

Upon irradiation of the eyeball 111 with the detection light, part of the detection light is reflected by an iris 112, and the light from the iris 112 enters the stereo camera apparatus 102. Upon irradiation of the eyeball 111 with the detection light, a cornea reflection image 113 as a virtual image of a cornea is formed on the eyeball 111, and the light from the cornea reflection image 113 enters the stereo camera apparatus 102.

Appropriately setting a relative position between the first camera 102A and the second camera 102B and the first light source 103A and the second light source 103B decreases the intensity of the light entering the stereo camera apparatus 102 from the iris 112, while increasing the intensity of the light entering the stereo camera apparatus 102 from the cornea reflection image 113. That is, an image of the iris 112 acquired by the stereo camera apparatus 102 is low in luminance, whereas an image of the cornea reflection image 113 is high in luminance. The stereo camera apparatus 102 can detect a position of the iris 112 and a position of the cornea reflection image 113 based on the luminance of the acquired image.

Figure 2:
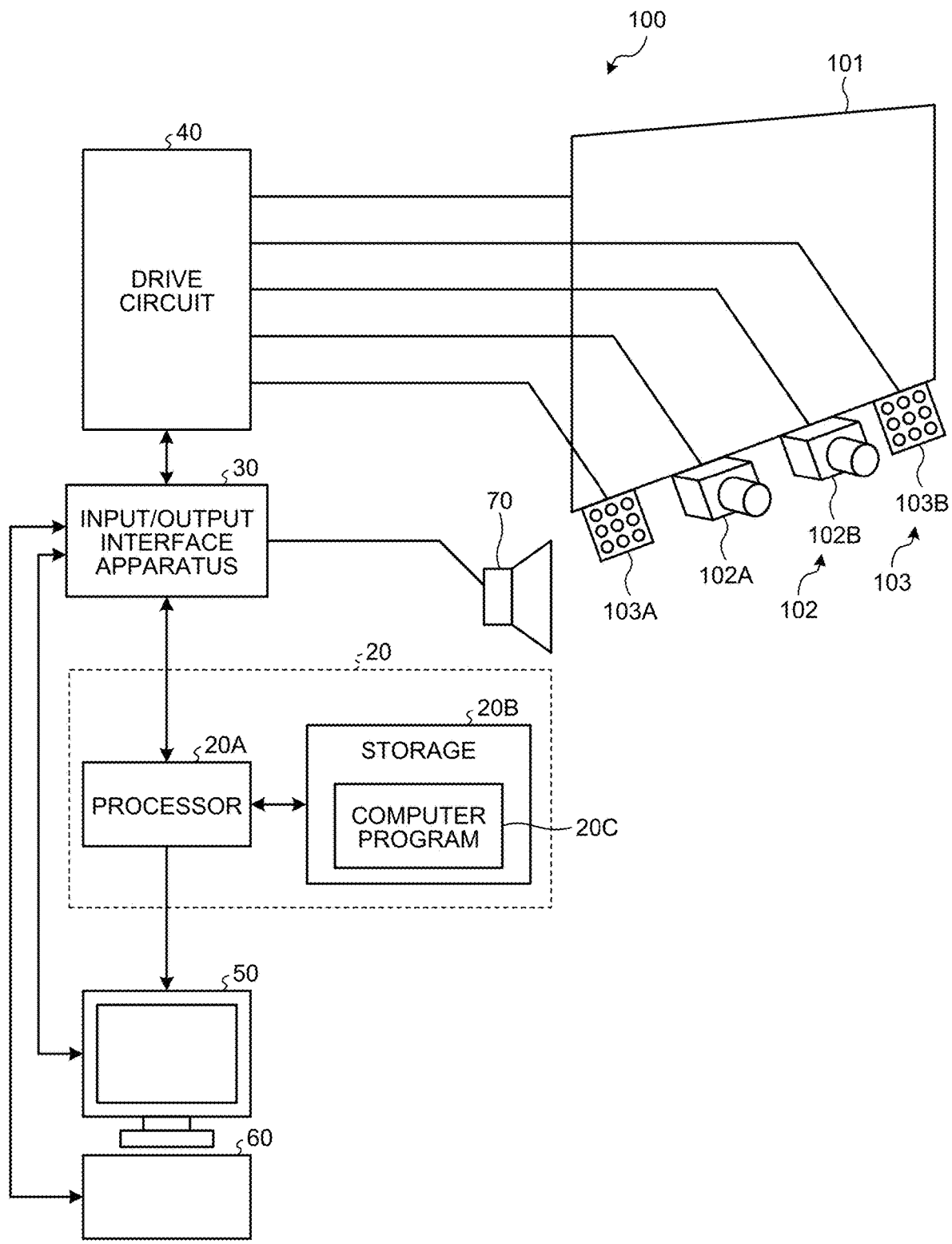
FIG. 2 is a diagram illustrating a hardware configuration example of the visual function detection apparatus according to the present embodiment.

FIG. 2 is a diagram illustrating a hardware configuration example of the visual function detection apparatus 100 according to the present embodiment. As illustrated in FIG. 2, the visual function detection apparatus 100 includes the display apparatus 101, the stereo camera apparatus 102, the illumination apparatus 103, a computer system 20, an input/output interface apparatus 30, a drive circuit 40, an output apparatus 50, and an input apparatus 60.

The computer system 20, the drive circuit 40, the output apparatus 50, and the input apparatus 60 perform data communication via the input/output interface apparatus 30. The computer system 20 includes a processor 20A and a storage 20B. The processor 20A includes a microprocessor such as a central processing unit (CPU). The storage 20B includes memories such as a read only memory (ROM) and random access memory (RAM) or a storage. The processor 20A performs processing in accordance with a computer program 20C stored in the storage 20B. The processor 20A executes the computer program 20C stored in the storage 20B to execute line-of-sight detection processing and thus can also serve as a line-of-sight detection apparatus according to the present embodiment.

The drive circuit 40 generates drive signals and outputs them to the display apparatus 101, the stereo camera apparatus 102, and the illumination apparatus 103. The drive circuit 40 supplies the image data of the eyeball 111 acquired by the stereo camera apparatus 102 to the computer system 20 via the input/output interface apparatus 30.

The output apparatus 50 includes a display apparatus such as a flat panel display. The output apparatus 50 may include a printing apparatus. The input apparatus 60 generates input data by being operated. The input apparatus 60 includes a keyboard or a mouse for a computer system. The input apparatus 60 may include a touch sensor provided on a display screen of the output apparatus 50 as the display apparatus.

In the present embodiment, the display apparatus 101 and the computer system 20 are separate apparatuses. The display apparatus 101 and the computer system 20 may be integral with each other. When the visual function detection apparatus 100 includes a tablet personal computer, for example, the tablet personal computer may come with the computer system 20, the input/output interface apparatus 30, the drive circuit 40, and the display apparatus 101.

Figure 3:
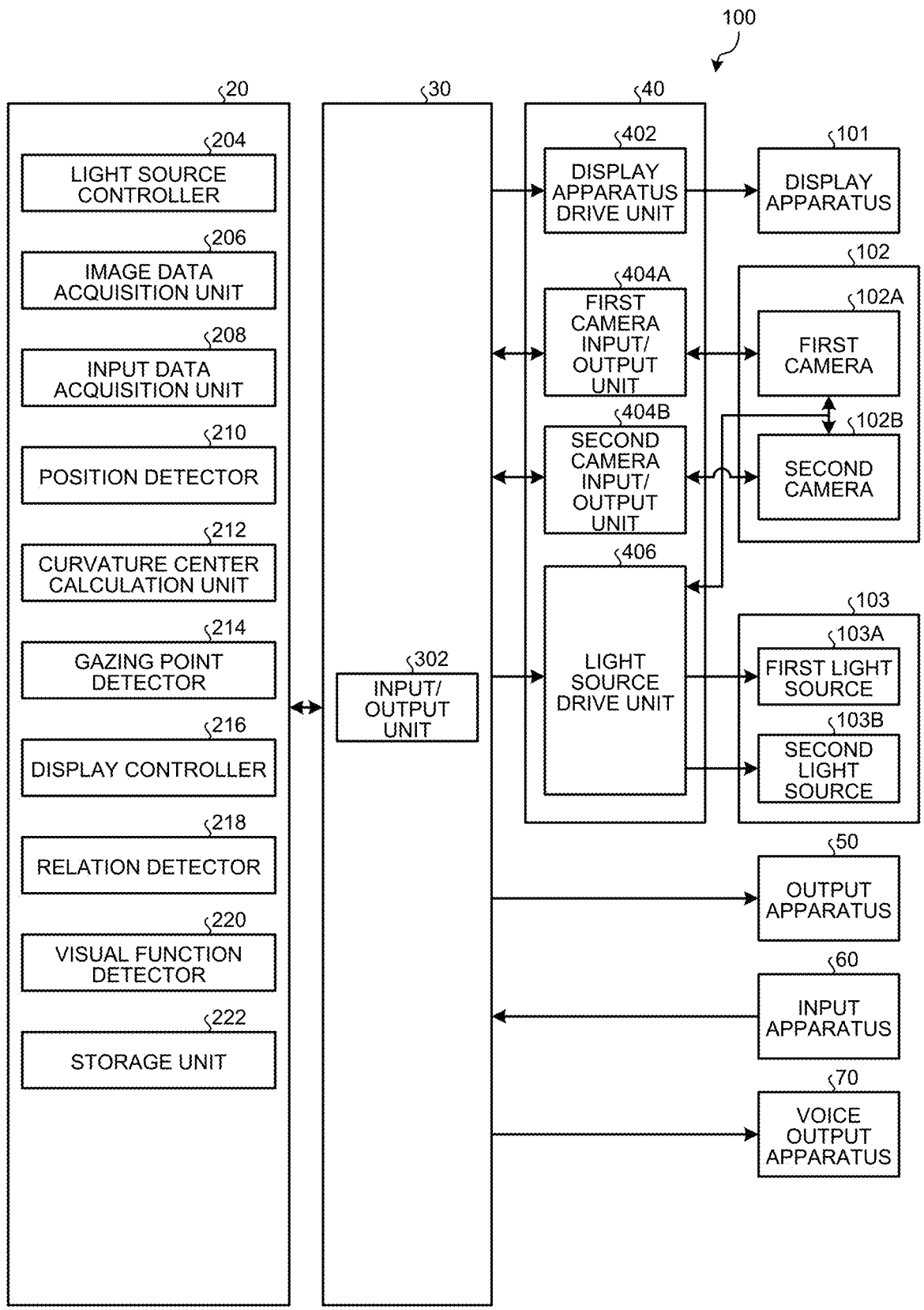
FIG. 3 is a functional block diagram illustrating an example of the visual function detection apparatus according to the present embodiment.

FIG. 3 is a functional block diagram illustrating an example of the visual function detection apparatus 100 according to the present embodiment. As illustrated in FIG. 3, the input/output interface apparatus 30 has an input/output unit 302. The drive circuit 40 includes: a display apparatus drive unit 402 that generates a drive signal to drive the display apparatus 101 to output the drive signal to the display apparatus 101; a first camera input/output unit 404A that generates a drive signal for driving the first camera 102A to output the drive signal to the first camera 102A; a second camera input/output unit 404B that generates a drive signal for driving the second camera 102B to output the drive signal to the second camera 102B; and a light source drive unit 406 that generates drive signals for driving the first light source 103A and the second light source 103B to output the drive signals to the first light source 103A and the second light source 103B. The first camera input/output unit 404A supplies the image data of the eyeball 111 acquired by the first camera 102A to the computer system 20 via the input/output unit 302. The second camera input/output unit 404B supplies the image data of the eyeball 111 acquired by the second camera 102B to the computer system 20 via the input/output unit 302.

The computer system 20 controls the visual function detection apparatus 100. The computer system 20 includes a light source controller 204, an image data acquisition unit 206, an input data acquisition unit 208, a position detector 210, a curvature center calculation unit 212, a gazing point detector 214, a display controller 216, a relation detector 218, a visual function detector 220, and a storage unit 222. The function of the computer system 20 is exhibited by the processor 20A and the storage 20B.

The light source controller 204 controls the light source drive unit 406 to control operating states of the first light source 103A and the second light source 103B. The light source controller 204 controls the first light source 103A and the second light source 103B such that the first light source 103A and the second light source 103B emit the detection light at different timings.

The image data acquisition unit 206 acquires the image data of the eyeball 111 of the test subject acquired by the stereo camera apparatus 102 including the first camera 102A and the second camera 102B from the stereo camera apparatus 102 via the input/output unit 302.

The input data acquisition unit 208 acquires the input data generated by the input apparatus 60 being operated from the input apparatus 60 via the input/output unit 302.

The position detector 210 detects position data of an iris center based on the image data of the eyeball 111 acquired by the image data acquisition unit 206. Further, the position detector 210 detects position data of a cornea reflection center based on the image data of the eyeball 111 acquired by the image data acquisition unit 206. The iris center is the center of the iris 112. The cornea reflection center is the center of the cornea reflection image 113. The position detector 210 detects the position data of the iris center and the position data of the cornea reflection center for each of right and left eyeballs 111 of the test subject.

The curvature center calculation unit 212 calculates position data of a cornea curvature center of the eyeball 111 based on the image data of the eyeball 111 acquired by the image data acquisition unit 206.

The gazing point detector 214 detects position data of a gazing point of the test subject based on the image data of the eyeball 111 acquired by the image data acquisition unit 206. In the present embodiment, the position data of the gazing point refers to position data of a point of intersection of a line-of-sight vector of the test subject and the display screen 101S of the display apparatus 101 defined in the three-dimensional global coordinate system. The gazing point detector 214 detects a line-of-sight vector of each of the right and left eyeballs 111 of the test subject based on the position data of the iris center and the position data of the cornea curvature center acquired from the image data of the eyeball 111. After the line-of-sight vector is detected, the gazing point detector 214 detects the position data of the gazing point indicating the point of intersection of the line-of-sight vector and the display screen 101S.

The display controller 216 outputs data to at least either the display apparatus 101 or the output apparatus 50. In the present embodiment, the display controller 216 outputs data for causing the display apparatus 101 to display the image 231 for determination to the display apparatus 101 to display the image 231 for determination on the display screen 101S of the display apparatus 101. The image 231 for determination displayed by the display controller 216 will be described below. The display controller 216 may cause the display screen 101S or the output apparatus 50 to display the position of the gazing point of each of the right and left eyeballs 111 of the test subject H.

The relation detector 218 detects relation information as information indicating a relation between a direction in which the image 231 for determination on the display screen 101S moves and a direction in which the gazing point detected by the gazing point detector 214 moves. A method of detecting the relation information will be described below.

The visual function detector 220 detects a visual function of the test subject H based on the relation information detected by the relation detector 218. The visual function detector 220 detects the visual function by deriving information as a criterion for determining whether the image 231 for determination is seen by the test subject H based on the relation information. That is, detecting the visual function here can be said to be deriving information as a criterion of determination whether the image 231 for determination can be visually recognized. The visual function detector 220 may derive information as a criterion for determining the eyesight of the test subject or derive information as a criterion for determining whether the test subject has cataract, for example, based on the determination whether the image 231 for determination is seen by the test subject H.

The storage unit 222 stores, for example, the image data of the eyeball 111 of the test subject H acquired by the image data acquisition unit 206, the position data of the gazing point detected by the gazing point detector 214, image data of the image (the image 231 for determination, for example) displayed on the display screen 101S, the relation information detected by the relation detector 218, data on a detection result of the visual function by the visual function detector 220.

The storage unit 222 stores a computer program causing a computer to execute processing to display an image on the display screen 101S, processing to detect the position of the gazing point of the test subject H observing the display screen 101S, processing to detect the relation information between the direction in which the image 231 for determination moves and the direction in which the gazing point moves, and processing to detect the visual function based on the information.

Figure 4:
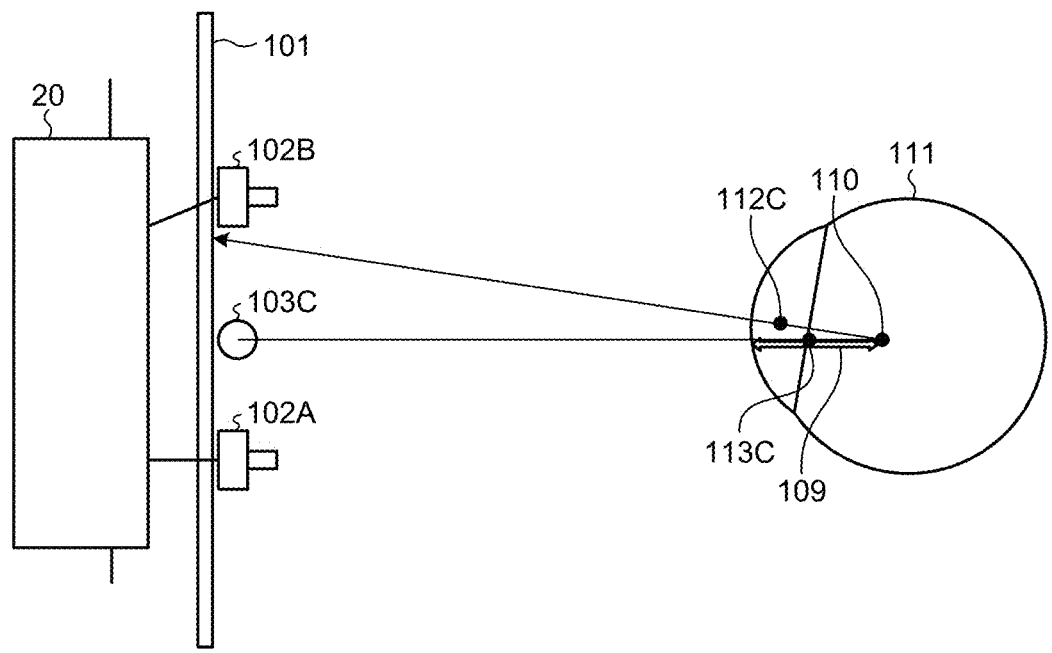
FIG. 4 is a schematic diagram for illustrating a method of calculating position data of a cornea curvature center according to the present embodiment.
Figure 5:
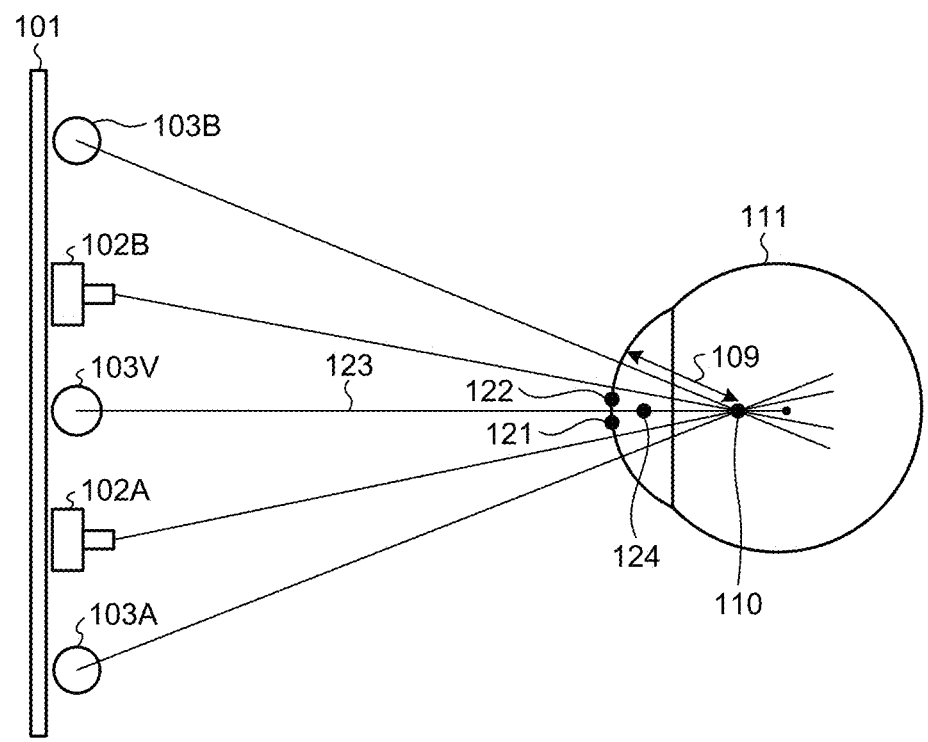
FIG. 5 is a schematic diagram for illustrating the method of calculating position data of a cornea curvature center according to the present embodiment.

The following describes an outline of processing by the curvature center calculation unit 212 according to the present embodiment. The curvature center calculation unit 212 calculates the position data of the cornea curvature center of the eyeball 111 based on the image data of the eyeball 111. FIG. 4 and FIG. 5 are schematic diagrams for illustrating a method of calculating position data of a cornea curvature center 110 according to the present embodiment. FIG. 4 illustrates an example in which the eyeball 111 is illuminated by one light source 103C. FIG. 5 illustrates an example in which the eyeball 111 is illuminated by the first light source 103A and the second light source 103B.

First, the following describes the example illustrated in FIG. 4. The light source 103C is placed between the first camera 102A and the second camera 102B. An iris center 112C is the center of the iris 112. A cornea reflection center 113C is the center of the cornea reflection image 113. In FIG. 4, the iris center 112C indicates an iris center when the eyeball 111 is illuminated by the one light source 103C. The cornea reflection center 113C indicates a cornea reflection center when the eyeball 111 is illuminated by the one light source 103C. The cornea reflection center 113C is present on a straight line connecting the light source 103C and the cornea curvature center 110. The cornea reflection center 113C is positioned at an intermediate point between a cornea surface and the cornea curvature center 110. A cornea curvature radius 109 is a distance between the cornea surface and the cornea curvature center 110. Position data of the cornea reflection center 113C is detected by the stereo camera apparatus 102. The cornea curvature center 110 is present on a straight line connecting the light source 103C and the cornea reflection center 113C. The curvature center calculation unit 212 calculates position data in which a distance from the cornea reflection center 113C on the straight line is a certain value as the position data of the cornea curvature center 110. The certain value is a value set in advance from a curvature radius value of a general cornea or the like and is stored in the storage unit 222.

The following describes the example illustrated in FIG. 5. In the present embodiment, the first camera 102A and the second light source 103B, and the second camera 102B and the first light source 103A are placed at positions laterally symmetric relative to a straight line passing through an intermediate position between the first camera 102A and the second camera 102B. It can be regarded that there is a virtual light source 103V at the intermediate position between the first camera 102A and the second camera 102B. A cornea reflection center 121 indicates a cornea reflection center in an image obtained by photographing the eyeball 111 with the second camera 102B. A cornea reflection center 122 indicates a cornea reflection center in an image obtained by photographing the eyeball 111 with the first camera 102A. A cornea reflection center 124 indicates a cornea reflection center corresponding to the virtual light source 103V. Position data of the cornea reflection center 124 is calculated based on position data of the cornea reflection center 121 and position data of the cornea reflection center 122 acquired by the stereo camera apparatus 102. The stereo camera apparatus 102 detects the position data of the cornea reflection center 121 and the position data of the cornea reflection center 122 in a three-dimensional local coordinate system defined in the stereo camera apparatus 102. Camera calibration by stereo calibration is performed on the stereo camera apparatus 102 in advance to calculate conversion parameters converting the three-dimensional local coordinate system of the stereo camera apparatus 102 into the three-dimensional global coordinate system. The conversion parameters are stored in the storage unit 222. The curvature center calculation unit 212 converts the position data of the cornea reflection center 121 and the position data of the cornea reflection center 122 acquired by the stereo camera apparatus 102 into position data in the three-dimensional global coordinate system using the conversion parameters. The curvature center calculation unit 212 calculates the position data of the cornea reflection center 124 in the three-dimensional global coordinate system based on the position data of the cornea reflection center 121 and the position data of the cornea reflection center 122 defined in the three-dimensional global coordinate system. The cornea curvature center 110 is present on a straight line 123 connecting the virtual light source 103V and the cornea reflection center 124. The curvature center calculation unit 212 calculates position data in which a distance from the cornea reflection center 124 on the straight line 123 is a certain value as the position data of the cornea curvature center 110. The certain value is a value set in advance from a curvature radius value of a general cornea or the like and is stored in the storage unit 222.

Thus, even when there are two light sources, the cornea curvature center 110 can be calculated by a method similar to the method when there is one light source.

The cornea curvature radius 109 is a distance between the cornea surface and the cornea curvature center 110. Consequently, position data of the cornea surface and the position data of the cornea curvature center 110 are calculated, whereby the cornea curvature radius 109 is calculated.

Figure 6:
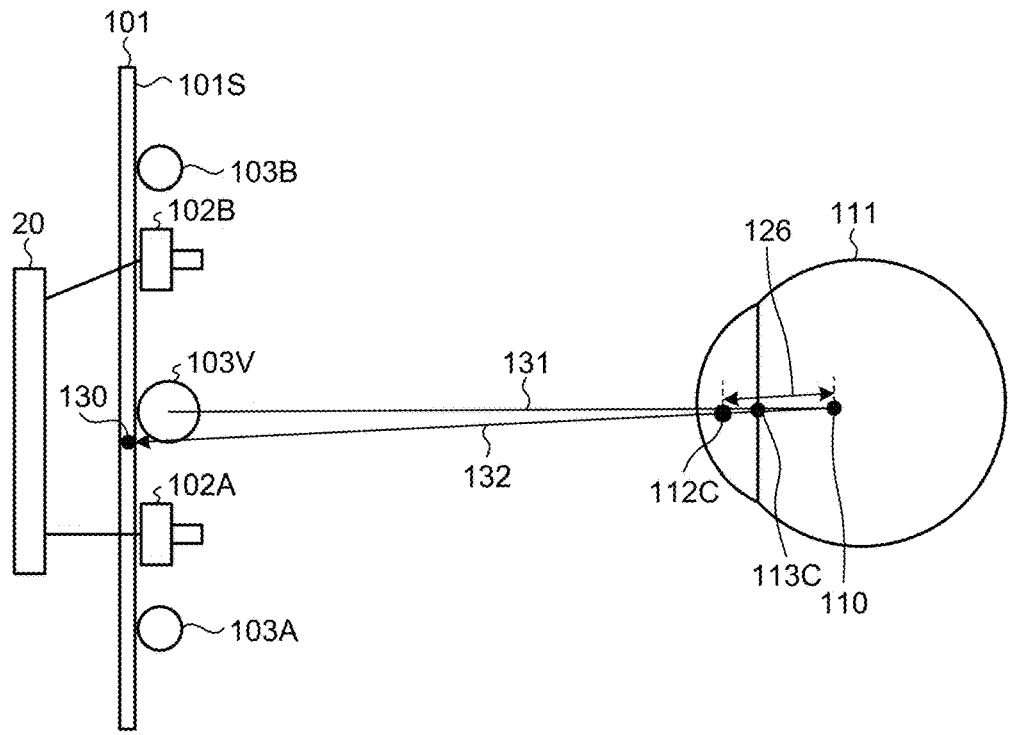
FIG. 6 is a schematic diagram for illustrating an example of calibration processing according to the present embodiment.

The following describes an exemplary method of detecting a line of sight according to the present embodiment. FIG. 6 is a schematic diagram for illustrating an example of calibration processing according to the present embodiment. In the calibration processing, a target position 130 is set in order to cause the test subject to gaze it. The target position 130 is defined in the three-dimensional global coordinate system. In the present embodiment, the target position 130 is set at a central position of the display screen 101S of the display apparatus 101, for example. The target position 130 may be set at an end position of the display screen 101S. An output controller 226 displays a target image at the set target position 130. A straight line 131 is a straight line connecting the virtual light source 103V and the cornea reflection center 113C. A straight line 132 is a straight line connecting the target position 130 and the iris center 112C. The cornea curvature center 110 is a point of intersection of the straight line 131 and the straight line 132. The curvature center calculation unit 212 can calculate the position data of the cornea curvature center 110 based on position data of the virtual light source 103V, position data of the target position 130, position data of the iris center 112C, and position data of the cornea reflection center 113C.

Figure 7:
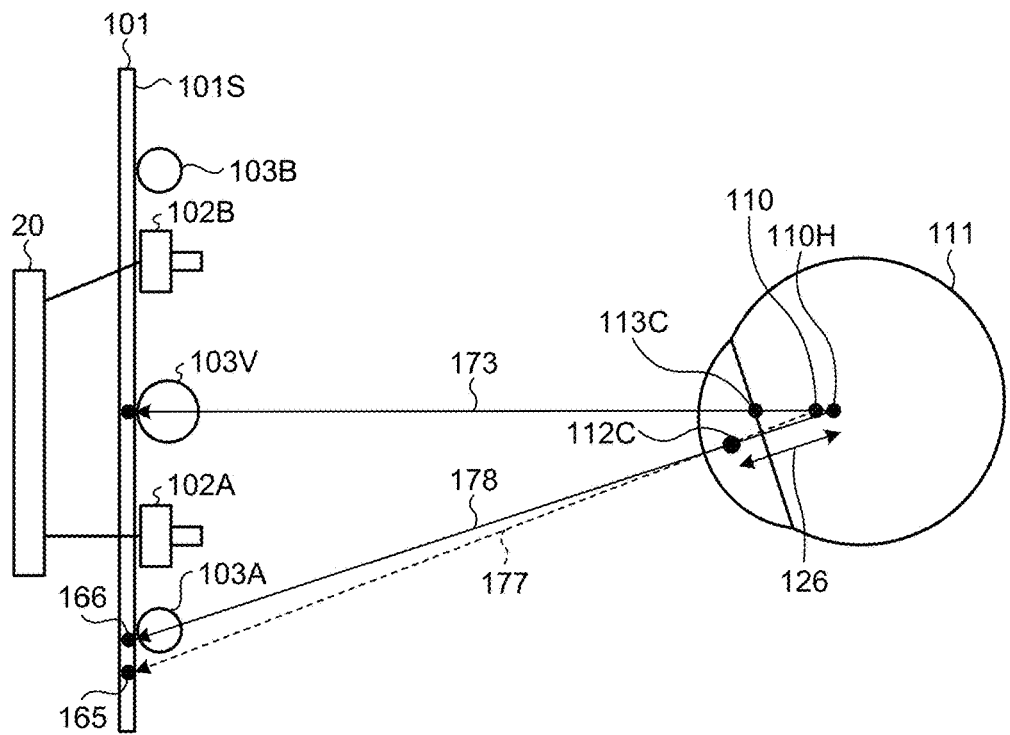
FIG. 7 is a schematic diagram for illustrating an example of gazing point detection processing according to the present embodiment.

The following describes gazing point detection processing. The gazing point detection processing is performed after the calibration processing. The gazing point detector 214 calculates the line-of-sight vector of the test subject and the position data of the gazing point based on the image data of the eyeball 111. FIG. 7 is a schematic diagram for illustrating an example of gazing point detection processing according to the present embodiment. In FIG. 7, a gazing point 165 indicates a gazing point determined from a cornea curvature center calculated using a general curvature radius value. A gazing point 166 indicates a gazing point determined from a cornea curvature center calculated using a distance 126 determined by the calibration processing. The iris center 112C indicates an iris center calculated in the calibration processing, whereas the cornea reflection center 113C indicates a cornea reflection center calculated in the calibration processing. A straight line 173 is a straight line connecting the virtual light source 103V and the cornea reflection center 113C. The cornea curvature center 110 is in a position of a cornea curvature center calculated from the general curvature radius value. The distance 126 is a distance between the iris center 112C calculated by the calibration processing and the cornea curvature center 110. A cornea curvature center 110H indicates a position of a corrected cornea curvature center obtained by correcting the cornea curvature center 110 using the distance 126. The cornea curvature center 110H is determined by the presence of the cornea curvature center 110 on the straight line 173 and the distance between the iris center 112C and the cornea curvature center 110 being the distance 126. Thus, a line of sight 177 calculated when the general curvature radius value is used is corrected to a line of sight 178. The gazing point on the display screen 101S of the display apparatus 101 is corrected from the gazing point 165 to the gazing point 166.

(Method of Detecting Visual Function)

Figure 8:
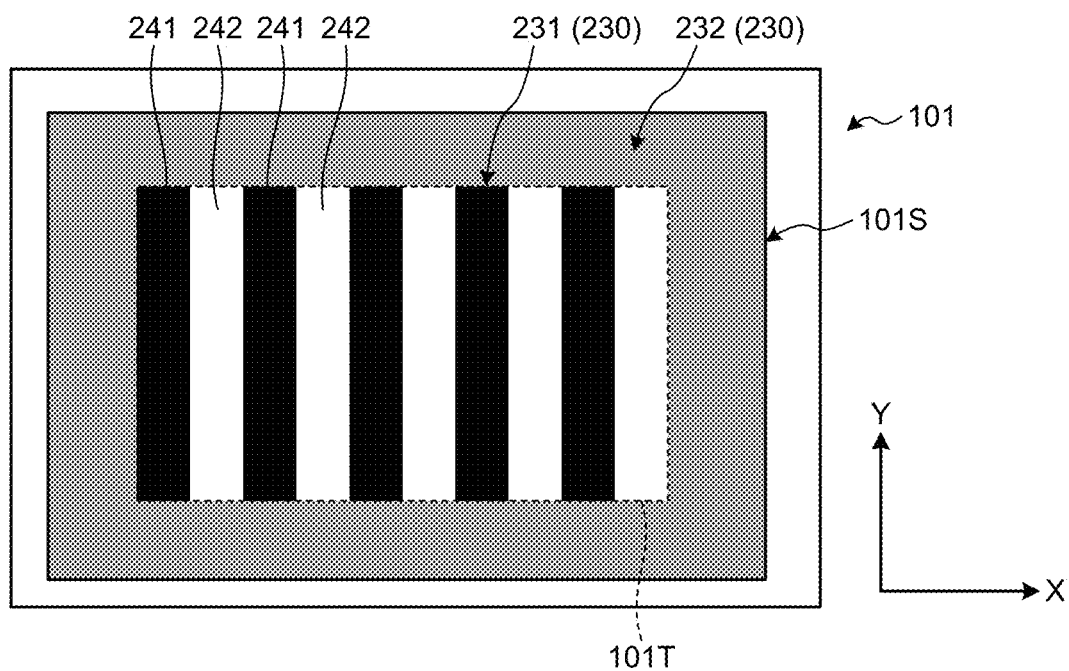
FIG. 8 is a diagram illustrating an image for determination according to the present embodiment.

That is The following describes a method of detecting a visual function according to the present embodiment. FIG. 8 is a diagram illustrating an image for determination according to the present embodiment. When the visual function detection is performed, the display controller 216 outputs data for causing the display apparatus 101 to display an image 230 to the display apparatus 101 to display the image 230 on the display screen 101S of the display apparatus 101. As illustrated in FIG. 8, the image 230 includes the image 231 for determination and an image 232 for background. That is, it can be said that the display controller 216 outputs data for causing the display apparatus 101 to display the image 231 for determination and data for causing the display apparatus 101 to display the image 232 for background, thereby causing the image 231 for determination and the image 232 for background to be displayed on the display screen 101S of the display apparatus 101. While the image 230 is an image occupying the entire region of the display screen 101S, it may be an image occupying part of the display screen 101S.

As illustrated in FIG. 8, the image 231 for determination is displayed within a display region 101T within a region in which the image 230 is displayed (the display screen 101S in this example). That is, the image 231 for determination is displayed so as to occupy the entire region of the display region 101T of the display screen 101S. In the present embodiment, the display region 101T is a partial region of the display screen 101S. However, the display region 101T may occupy the entire region of the display screen 101S. In this case, the image 230 does not include the image 232 for background and includes only the image 231 for determination.

The image 231 for determination is preferably equal to one time or less than the display screen 101S. Thus, the test subject H can appropriately visually recognize the image 231 for determination.

The image 231 for determination is an image displaying a pattern. Specifically, the image 231 for determination includes first images 241 and second images 242. In other words, the display region 101T is sectioned into a first region, in which the first images 241 are displayed, and a first region, in which the second images 242 are displayed. Consequently, the first images 241 can also be referred to as the first region, in which the first images 241 are displayed, whereas the second images 242 can also be referred to as the second region, in which the second images 242 are displayed. The first images 241 and the second images 242 are images different from each other in luminance. In the present embodiment, the first images 241 are images lower in luminance than the second images 242. In the example of the present embodiment, the first images 241 and the second images 242 are gray images. Consequently, the first images 241 have more black components than the second images 242, whereas the second images 242 have more white components than the first images 241. However, the first images 241 and the second images 242 may be colored images so long as they are images different from each other in luminance.

As illustrated in FIG. 8, in the present embodiment, the image 231 for determination includes a plurality of first images 241 and second images 242, in which the first images 241 and the second images 242 are arranged alternately in stripes. That is, the first images 241 and the second images 242 have a length along the Y-axial direction the same as a length of the display region 101T along the Y-axial direction and extend from an upper end to a lower end of the display region 101T along the Y-axial direction. The first images 241 and the second images 242 have a length (width) along the X-axial direction shorter than a length of the display region 101T along the X-axial direction. The first images 241 and the second images 242 are alternately arranged along the X-axial direction within the display region 101T. In the present embodiment, the first images 241 separate from end faces of the display region 101T along the X-axial direction are equal to each other in area. Similarly, the second images 242 separate from the end faces of the display region 101T along the X-axial direction are also equal to each other in area. The first images 241 and the second images 242 separate from the end faces of the display region 101T along the X-axial direction are also equal to each other in area. The number of the first images 241 and the number of the second images 242 are also equal to each other. However, the first images 241 may be different from each other in area and shape, and the second images 242 may be different from each other in area and shape. The number of the first images 241 and the number of the second images 242 may also be different from each other.

As illustrated in FIG. 8, the image 232 for background is an image displayed in a region other than the display region 101T in which the image 231 for determination is displayed within the region in which the image 230 is displayed (the display screen 101S in this example). That is, the image 232 for background is an image displayed so as to surround the display region 101T (the image 231 for determination). The image 232 for background is displayed so as to occupy the entire region other than the display region 101T in the region in which the image 230 is displayed. However, the image 232 for background only needs to surround the display region 101T, and may occupy part of the region other than the display region 101T.

The image 231 for determination is a uniform image with no pattern. In the present embodiment, the image 232 for background is an image with constant luminance across the entire region and is further an image having the same color as that of the image 231 for determination, i.e., a gray image. Consequently, the image 232 for background is higher in luminance and has more white components than the first images 241. The image 232 for background is lower in luminance and has more black components than the second images 242.

Figure 9:
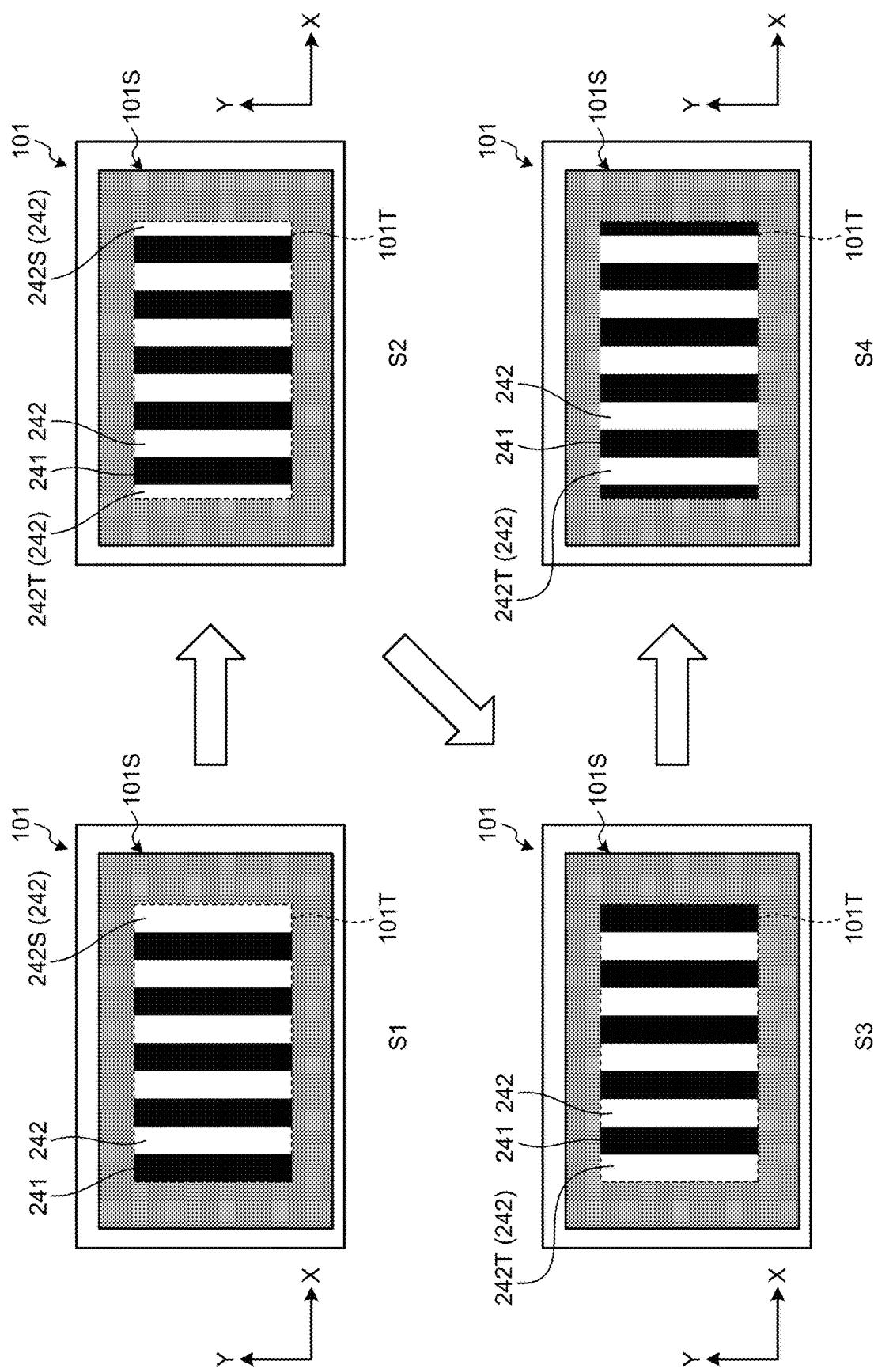
FIG. 9 is a diagram illustrating how the image for determination moves.

FIG. 9 is a diagram illustrating how the image for determination moves. The display controller 216 moves the image 231 for determination in the X-axial direction within the display region 101T. The display controller 216 moves the image 231 for determination in the X-axial direction within the display region 101T with the position of the display region 101T fixed. That is, the image 231 for determination can be said to be a moving image displayed within the display region 101T. The direction in which the image 231 for determination is moved is not limited to the X-axial direction, may be any direction, and may be a certain direction as one direction set in advance. While the certain direction is preferably a direction in which the first images 241 and the second images 242 are arranged as in the present embodiment, the certain direction is not limited thereto. The direction in which the image 231 for determination is moved is not limited to the certain direction and the display controller 216 may move the image 231 for determination in any direction. That is, the display controller 216 only needs to move the image 231 for determination in the display region 101T. The display controller 216 preferably does not switch the direction in which the image 231 for determination is moved in mid-course. The display controller 216 may move the position of the display region 101T.

More specifically, the display controller 216 scrolls the image 231 for determination, i.e., the first images 241 and the second images 242 along the X-axial direction. In other words, the display controller 216 prepares a plurality of the images 231 for determination in advance. Those images 231 for determination are images in which display positions of the first images 241 and the second images 242 deviate from each other along the X-axial direction (images at states S1 to S4 in FIG. 9, for example). The display controller 216 displays these images 231 for determination in order for each frame. Thus, the image 231 for determination is visually recognized as a moving image in which the first images 241 and the second images 242 are scrolled along the X-axial direction. In this case, the first images 241 and the second images 242 move in the X-axial direction within the display region 101T with the lapse of time, upon reaching the end face of the display region 101T in the X-axial direction, gradually reduce in size, and disappear from the display region 101T. The first images 241 and the second images 242 then successively appear from the end opposite to the X-axial direction and, upon reaching a certain area, move in the X-axial direction.

Even more specifically, as illustrated in FIG. 9, attention is paid on a second image 242S as one of the second images 242. The second image 242S moves in the X-axial direction within the display region 101T with the lapse of time to reach an end of the display region 101T in the X-axial direction (the right end in the example in FIG. 9) (the state S1 in FIG. 9). Subsequently, the second image 242S gradually reduces in area at the end in the X-axial direction (the state S2 in FIG. 9) and, with a further lapse of time, disappears from the display region 101T (the state S3 in FIG. 9). During the movement of the second image 242, at an end of the display region 101T opposite to the X-axial direction (the left end in the example in FIG. 9), another second image 242I appears while gradually increasing in area toward the X-axial direction (the state S2) and, upon reaching a set area (the state S3), moves in the X-axial direction within the display region 101T while keeping its area (the state S4). The first images 241 also move like the second images 242S and 242T. Upon reaching this state S4, the image 231 for determination returns to the state S1 and repeats the same movement. That is, while the display controller 216 moves the image 231 for determination in the X-axial direction, the image 231 for determination repeats such movement.

The display controller 216 moves the image 231 for determination at a speed set in advance for each frame. While a moving speed is about 100 pixels/second or more and 400 pixels/second or less, the moving speed is not limited thereto, and can be set to any moving speed.

Figure 10:
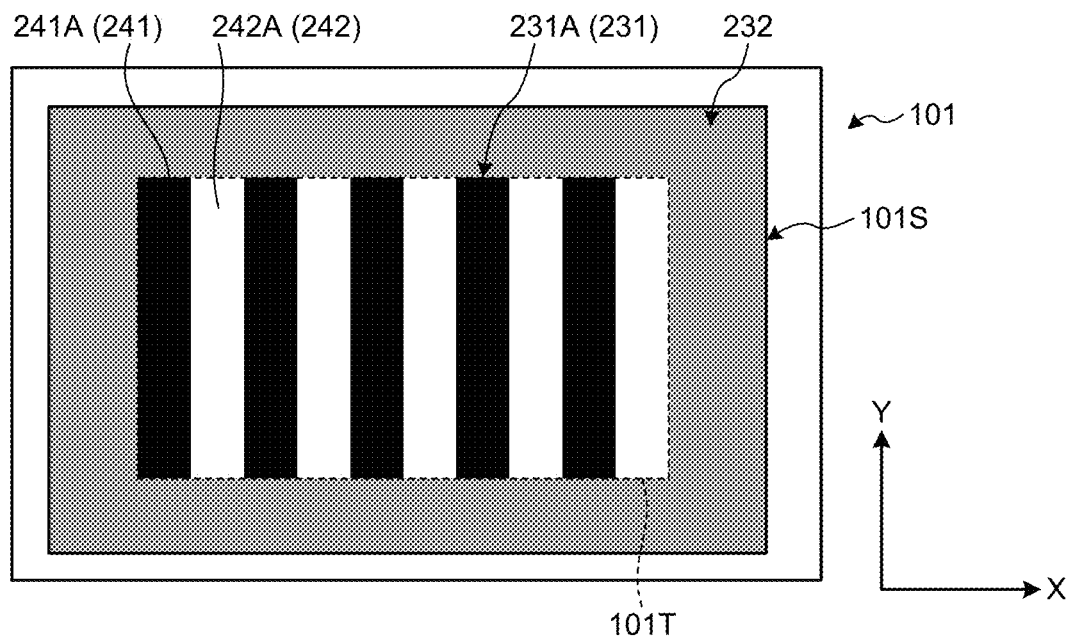
FIG. 10 is a diagram illustrating the image for determination with a different pattern.
Figure 11:
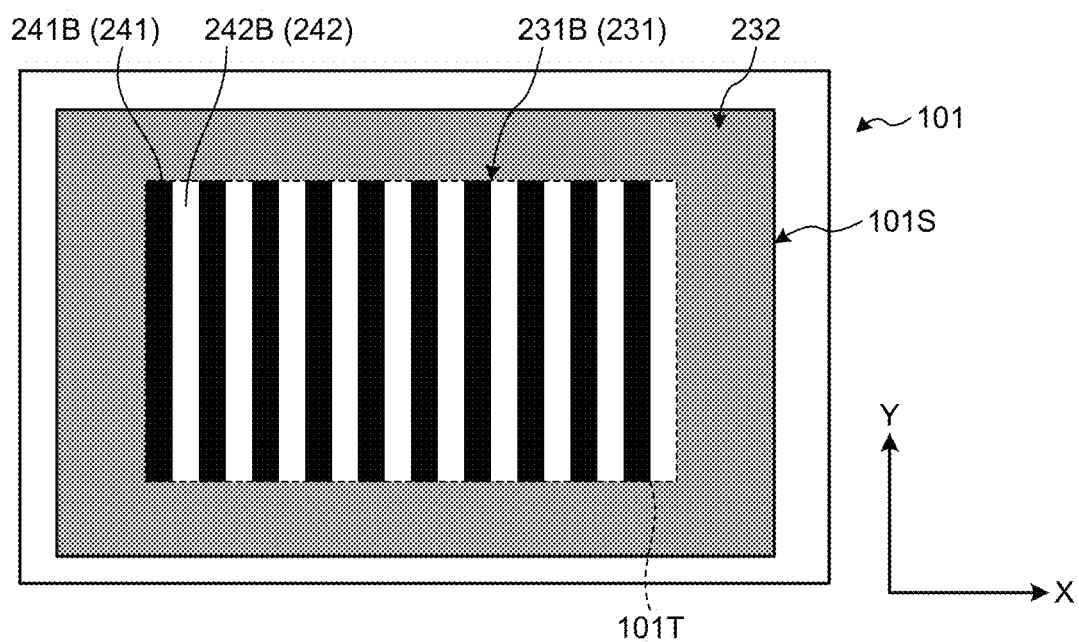
FIG. 11 is a diagram illustrating the image for determination with a different pattern.
Figure 12:
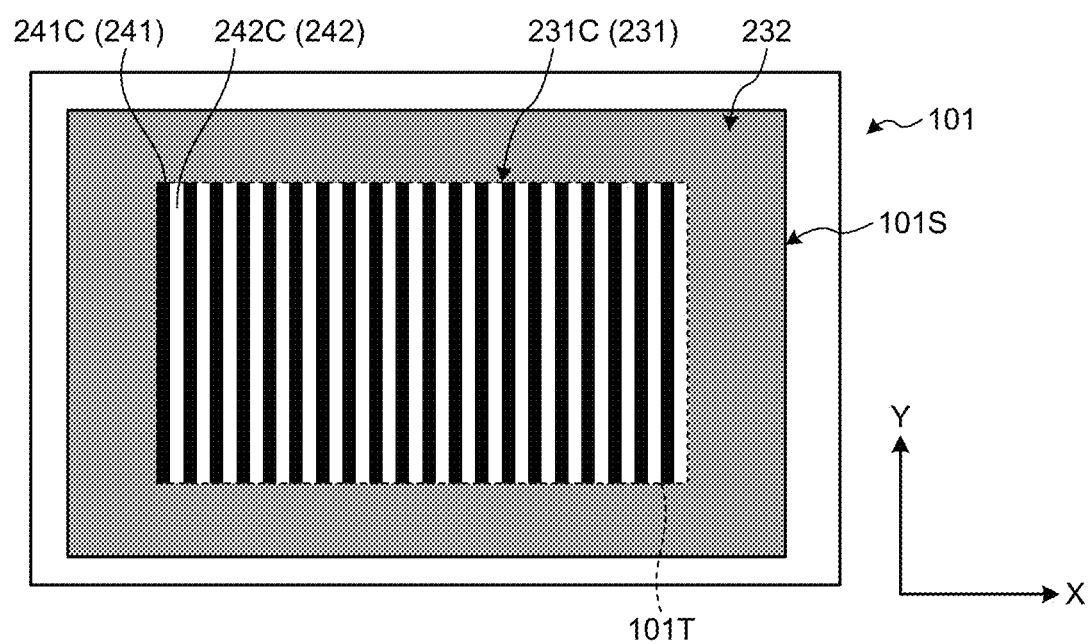
FIG. 12 is a diagram illustrating the image for determination with a different pattern.

FIG. 10 to FIG. 12 are diagrams illustrating the images for determination with different patterns. The display controller 216 may display the image 231 for determination with different patterns as illustrated in FIG. 10 to FIG. 12, for example, for a visual function detection examination. The display controller 216 selects the image 231 for determination with any pattern and moves the image 231 for determination with the selected pattern as described above.

An image 231A for determination illustrated in FIG. 10, an image 231B for determination illustrated in FIG. 11, and an image 231C for determination illustrated in FIG. 12 are different from each other in the size (area) of the first images 241 and the second images 242 and are also different from each other in the number of the first images 241 and the second images 242. That is, the images 231A, 231B, and 231C for determination are different from each other in the density distribution of the first images 241 and the second images 242. While the image 231A for determination, the image 231B for determination, and the image 231C for determination are equal to each other in the entire size, i.e., the size of the display region 101T, they may be different from each other in size.

In the examples in FIG. 10 to FIG. 12, first images 241B and second images 242B of the image 231B for determination are smaller in area than first images 241A and second images 242A of the image 231A for determination. Further, a length of the first images 241B and the second images 242B along the X-axial direction is shorter than a length of the first images 241A and the second images 242A along the X-axial direction. In the image 231B for determination, the number of the first images 241B and the second images 242B is larger than that of the first images 241A and the second images 242A of the image 231A for determination. First images 241C and second images 242C of the image 231C for determination are smaller in area than the first images 241B and the second images 242B of the image 231B for determination. Further, a length of the first images 241C and the second images 242C along the X-axial direction is shorter than a length of the first images 241B and the second images 242B along the X-axial direction. In the image 231C for determination, the number of the first images 241C and the second images 242C is larger than that of the first images 241B and the second images 242B of the image 231B for determination.

The image 231B for determination illustrated in FIG. 11, in which the first images 241 and the second images 242 are smaller than those of the image 231A for determination illustrated in FIG. 10, is more difficult for the test subject to visually recognize than the image 231A for determination. Similarly, the image 231C for determination illustrated in FIG. 11 is more difficult for the test subject to visually recognize than the image 231B for determination. Consequently, the display controller 216 thus displays the image 231 for determination with different patterns and can thereby detect the degree of the visual function (eyesight, for example) of the test subject H step by step.

When the visual function detection is performed, the display controller 216 thus causes the image 231 for determination and the image 232 for background to be displayed on the display screen 101S of the display apparatus 101. During the visual function detection, the test subject H observes the display screen 101S, and the gazing point detector 214 detects the gazing point 166 of the test subject H at that time. The relation detector 218 detects relation information indicating a relation between a moving direction of the image 231 for determination on the display screen 101S and a moving direction of the gazing point detected by the gazing point detector 214, and the visual function detector 220 detects the visual function of the subject H based on the relation information. The following describes the flow detecting the visual function.

Figure 13:
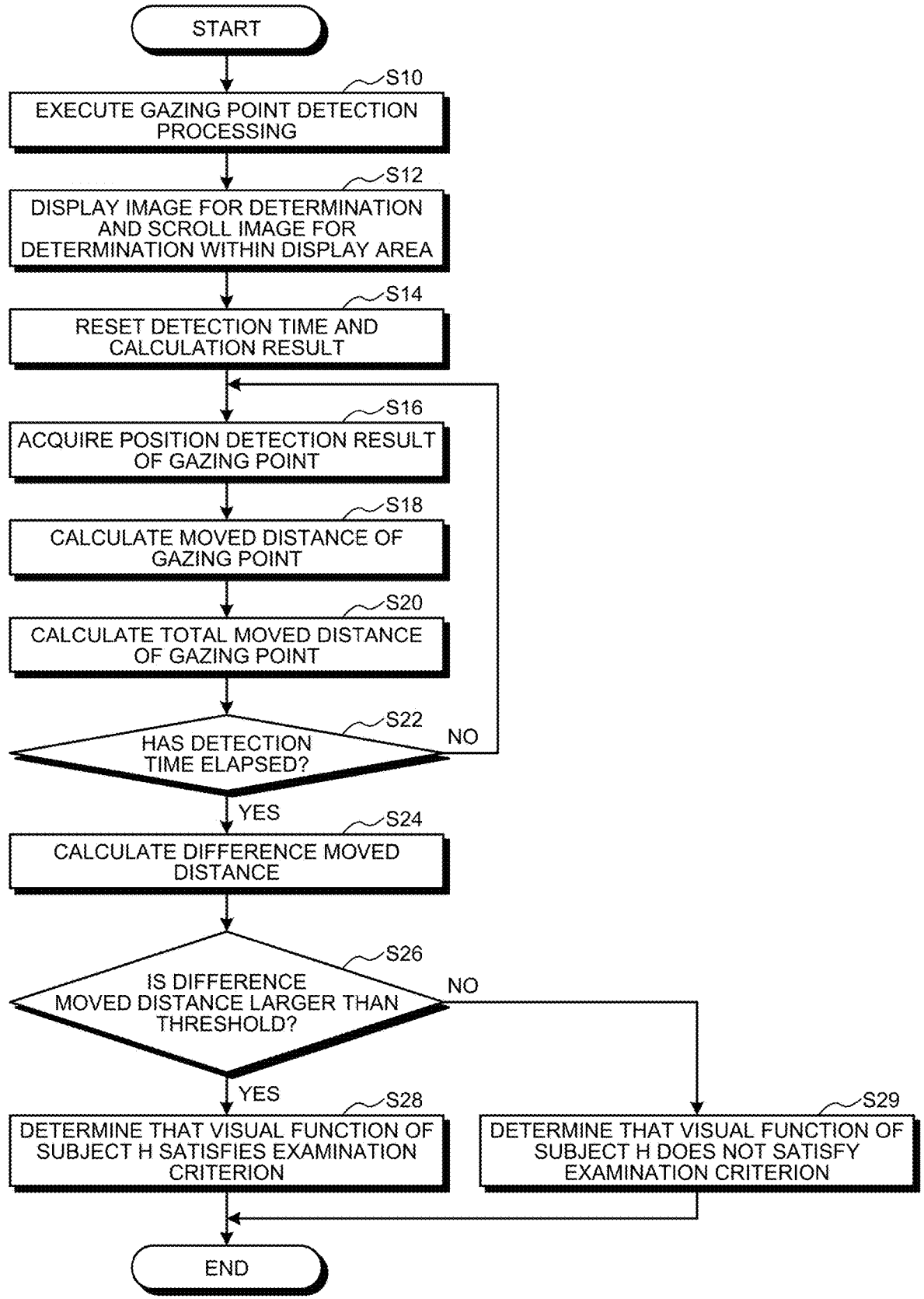
FIG. 13 is a flowchart illustrating the flow of detecting a visual function.
Figure 14:
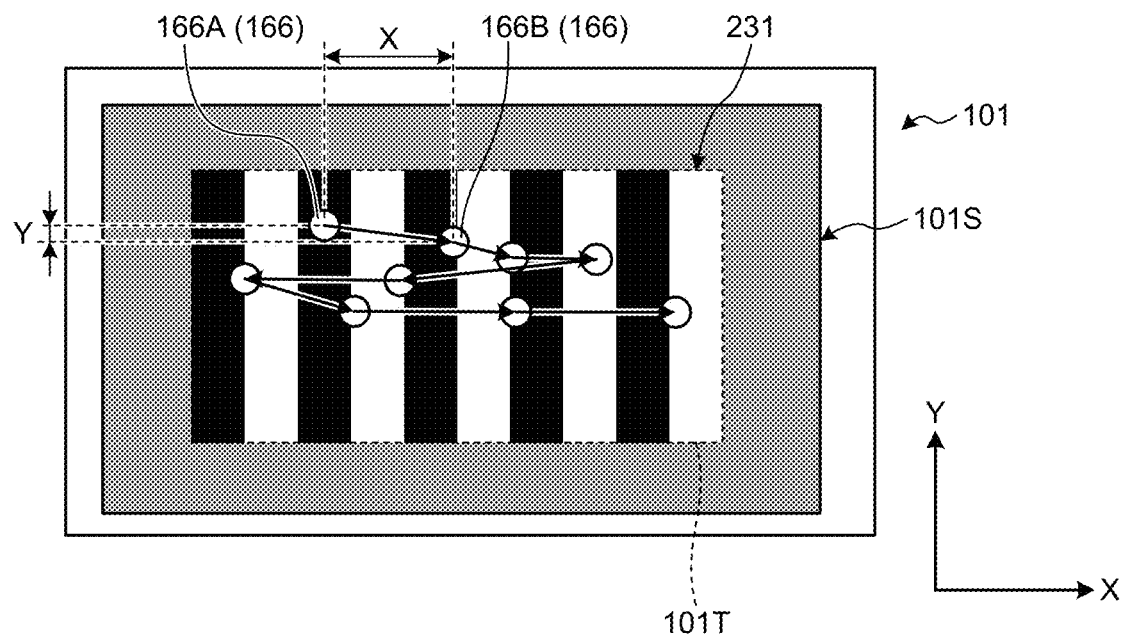
FIG. 14 is a diagram illustrating an example of a position of a gazing point.

FIG. 13 is a flowchart illustrating the flow of detecting the visual function. FIG. 14 is a diagram illustrating an example of the position of the gazing point. As illustrated in FIG. 13, when the visual function detection is performed, the gazing point detector 214 executes the gazing point detection processing described above (Step S10) to detect a position of the gazing point 166 of the test subject H positioned in front of the display screen 101S. The image data of the eyeball 111 of the test subject is acquired every certain time by photographing by the image data acquisition unit 206. Consequently, the gazing point detector 214 detects the position of the gazing point 166 every certain time. This certain time is about ¹⁄₆₀ second, for example, and thus the gazing point 166 is detected about 60 times per second. However, this certain time has any duration. The gazing point detector 214 continues position detection of the gazing point 166 over a period during which the image 231 for determination is displayed, which will be described below.

The visual function detection apparatus 100 displays the image 231 for determination on the display region 101T and scrolls (moves) the image 231 for determination within the display region 101T by the display controller 216 (Step S12). That is, the display controller 216 continues to display the image 231 for determination while scrolling it within the display region 101T. The visual function detection apparatus 100 then resets a detection time and a calculation result (Step S14) to acquire a position detection result of the gazing point 166 (Step S16). The detection time is a time set in advance and is a period during which the image 231 for determination is displayed to perform gazing point detection. While the detection time is about 20 seconds, for example, the time is any time. The visual function detection apparatus 100 resets the detection time, starts display of the image 231 for determination and the gazing point detection, and starts to count a time from the time of the start. The calculation result is a calculation result of a total moved distance described below and the like. That is, resetting the calculation result is making the value of an accumulated total moved distance zero, and the visual function detection apparatus 100 starts calculation of the total moved distance from this time. The visual function detection apparatus 100 performs position detection of the gazing point 166 by the gazing point detector 214 while the image 231 for determination is displayed on the display region 101T, and acquires the position detection result of the gazing point 166 for each detection of the gazing point 166.

Upon acquisition of the position detection result of the gazing point 166, the visual function detection apparatus 100 calculates a moved distance of the gazing point 166 by the relation detector 218 (Step S18). FIG. 14 is a diagram illustrating movement of the gazing point. The following describes calculation of a moved distance of a gazing point 166B as an example. A gazing point 166A in FIG. 14 is a gazing point detected immediately before the gazing point 166B. Upon acquisition of a position detection result of the gazing point 166B, i.e., coordinates of the gazing point 166B, the relation detector 218 calculates a distance between the gazing point 166B and the gazing point 166A as the moved distance. More specifically, the relation detector 218 calculates a distance X as a distance between the gazing point 166B and the gazing point 166A along the X-axial direction and a distance Y as a distance between the gazing point 166B and the gazing point 166A along the Y-axial direction. Thus, the relation detector 218 calculates the distance X and the distance Y with the length between the detected gazing point 166 and the gazing point 166 detected immediately before as the moved distance. The distance X can be said to be a vector component of the distance between the gazing point 166B and the gazing point 166A along the moving direction of the image 231 for determination, whereas the distance Y can be said to be a vector component of the distance between the gazing point 166B and the gazing point 166A in a direction orthogonal to the moving direction of the image 231 for determination. However, the distance X calculated in this example is not necessarily limited to the X-axial direction and may be any direction. That is, the distance X may be a vector component of the distance between the gazing point 166B and the gazing point 166A (the moved distance of the gazing point for each detection) along any direction (a first direction), whereas the distance Y may be a vector component of the distance between the gazing point 166B and the gazing point 166A along a direction orthogonal to any direction (the first direction).

After calculation of the moved distance of the gazing point 166, the visual function detection apparatus 100 calculates a total moved distance of the gazing point 166 by the relation detector 218 (Step S20). The relation detector 218 totals all the moved distances calculated so far to calculate the total moved distance. Consequently, the relation detector 218 adds the moved distance detected at this time to the total moved distance calculated at an immediately previous time to calculate the total moved distance. The relation detector 218 detects this total moved distance as the relation information. Specifically, the relation detector 218 calculates the total moved distance for the X-axial direction and the total moved distance for the Y-axial direction by Expressions (1) and (2) below.

$$XSUM = XSUM(-1) + X \quad (1)$$

$$YSUM = YSUM(-1) + Y \quad (2)$$

Where XSUM is the total moved distance for the X-axial direction, whereas XSUM(−1) is the total moved distance calculated at the immediately previous time. YSUM is the total moved distance for the Y-axial direction, whereas YSUM(−1) is the total moved distance calculated at the immediately previous time.

Upon calculation of the total moved distance, the visual function detection apparatus 100 determines whether the detection time has elapsed (Step S22). If the detection time has not elapsed (No at Step S22), the visual function detection apparatus 100 returns to Step S16 to repeat the subsequent processing. That is, the visual function detection apparatus 100 acquires positional information of the gazing point 166 detected at a next time to update the total moved distance. The visual function detection apparatus 100 repeats update of the total moved distance until the detection time elapses.

If the detection time has elapsed (Yes at Step S22), the visual function detection apparatus 100 calculates a difference moved distance by the visual function detector 220 (Step S24) and determines whether the difference moved distance is larger than a threshold (Step S26). The visual function detector 220 calculates a difference between the total moved distance XSUM for the X-axial direction and the total moved distance YSUM for the Y-axial direction as the difference moved distance and, based on this difference moved distance, performs determination whether the visual function of the test subject H satisfies an examination criterion. More specifically, the visual function detector 220 calculates a value obtained by subtracting the total moved distance YSUM from the total moved distance XSUM as the difference moved distance. The visual function detector 220 determines whether the difference moved distance is larger than a threshold set in advance. If the difference moved distance is larger than the threshold (Yes at Step S26), the visual function detector 220 determines that the visual function of the test subject H satisfies the examination criterion (Step S28). On the other hand, if the difference moved distance is not larger than the threshold (No at Step S26), i.e., the threshold or less, the visual function detector 220 determines that the visual function of the test subject H does not satisfy the examination criterion (Step S29). Whit Step S28 or S29, the present processing ends. The visual function detector 220 derives this determination result about whether the visual function of the test subject H satisfies the examination criterion as information as a criterion for detecting the visual function and stores the information in the storage unit 222, for example.

Figure 15:
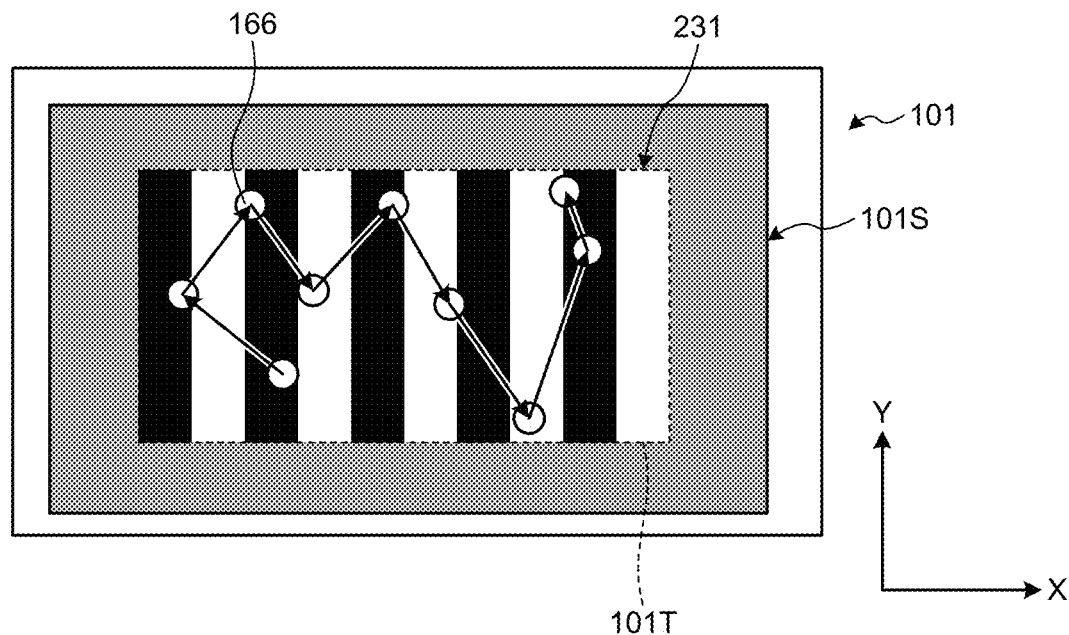
FIG. 15 is a diagram illustrating an example of the position of the gazing point.

FIG. 15 is a diagram illustrating an example of the position of the gazing point. FIG. 14 is an example when the test subject H can visually recognize the image 231 for determination, whereas FIG. 15 is an example when the test subject H cannot visually recognize the image 231 for determination. The image 231 for determination is a moving image moving in a certain direction (the X-axial direction in this example) within the display region 101T. Consequently, this image 231 for determination exhibits function like an optokinetic nystagmus (OKN) drum, such that when the test subject H can visually recognize the image 231 for determination, the image 231 for determination causes the eyeball 111 of the test subject H to reciprocate along the moving direction of the image 231 for determination (the X-axial direction in this example) while attracting the attention of the test subject H. Consequently, when the test subject H can visually recognize the image 231 for determination, the gazing point 166 has a trajectory reciprocating along the X-axial direction in correspondence with the movement of the image 231 for determination as in FIG. 14. On the other hand, when the test subject H cannot visually recognize the image 231 for determination, the gazing point 166 does not correspond to the movement of the image 231 for determination and tends not to have a trajectory reciprocating along the X-axial direction as in FIG. 15.

Figure 16:
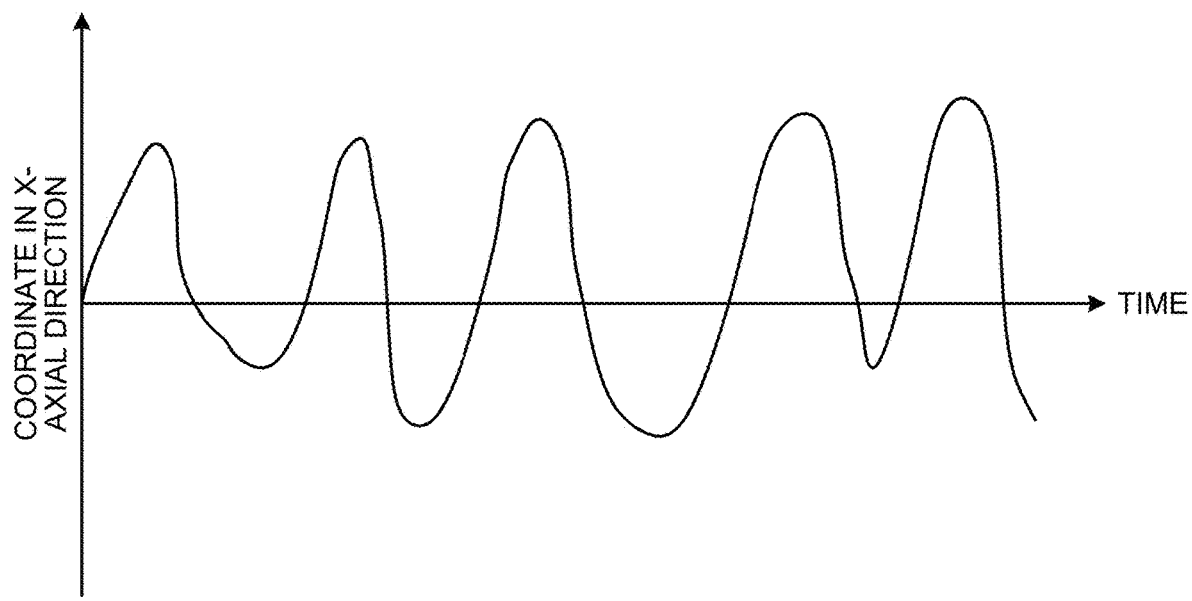
FIG. 16 is a graph illustrating an example of change in coordinate of the gazing point as time proceeds.
Figure 17:
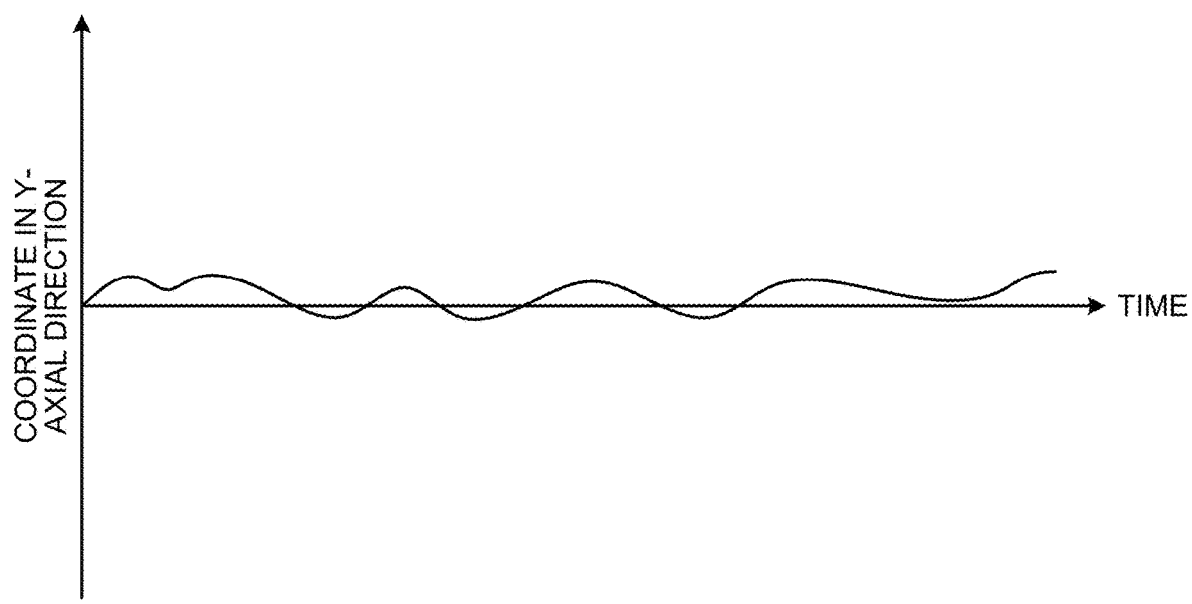
FIG. 17 is a graph illustrating an example of change in coordinate of the gazing point as time proceeds.

FIG. 16 and FIG. 17 are graphs each illustrating an example of change in coordinate of the gazing point as time proceeds. FIG. 16 illustrates an example of change in coordinate of the gazing point 166 in the X-axial direction when the test subject H can visually recognize the image 231 for determination, whereas FIG. 17 illustrates an example of change in coordinate of the gazing point 166 in the Y-axial direction when the test subject H can visually recognize the image 231 for determination. When the test subject H can visually recognize the image 231 for determination, the gazing point 166 tends to change in the coordinates as in FIG. 16 and FIG. 17. The visual function detector 220 according to the present embodiment calculates the difference moved distance by subtracting the total moved distance YSUM from the total moved distance XSUM to perform determination based on the difference moved distance and thus appropriately detects whether the gazing point 166 of the test subject H has a tendency like FIG. 16 and FIG. 17. Consequently, the visual function detection apparatus 100 can appropriately examine the visual function of the test subject.

In the present embodiment, the total moved distance is updated and calculated for each acquisition of the positional information of the gazing point 166. However, the relation detector 218 may calculate the total moved distance collectively after a lapse of the detection period.

The determination by the visual function detector 220 is not limited to the one based on the difference moved distance. Determination by the following method is also possible, for example. That is, the relation detector 218, upon acquisition of the position detection result of the gazing point 166 at Step S16, substitutes the position detection result into an array for each acquisition. That is, the relation detector 218 stores the positional information of the gazing point 166 for each timing. Upon a lapse of the detection period, the relation detector 218 calculates a moving average of the gazing point 166 in the X-axial direction and a moving average of the gazing point 166 in the Y-axial direction. The moving average is a value obtained by averaging certain data and data nearest to the certain data. In the present embodiment, a coordinate value of the gazing point 166 at a timing and coordinate values of the gazing point 166 nearest to that timing (an immediately previous timing and an immediately following timing, for example) are totaled, and the total is divided by the number of the totaled gazing point 166 to calculate the moving average. That is, the relation detector 218 totals the coordinate of the gazing point 166 in the X-axial direction and the coordinates of the gazing point 166 detected at the timings nearest to that gazing point 166 in the X-axial direction and divides the total by the number of the totaled gazing point 166 to calculate the moving average in the X-axial direction. The relation detector 218 totals the coordinate of the gazing point 166 in the Y-axial direction and the coordinates of the grazing point 166 detected at the timings nearest to that grazing point 166 in the Y-axial direction and divides the total by the number of the totaled gazing point 166 to calculate the moving average in the Y-axial direction. The relation detector 218 calculates the moving average in the X-axial direction and the moving average in the Y-axial direction for all the gazing points 166.

The relation detector 218 arranges the moving average in the X-axial direction and the moving average in the Y-axial direction for each of the gazing points 166 in a time series and extracts the number of times the moving direction is reversed. Reversing of the moving direction includes a case in which a coordinate moving toward a plus side with the lapse of time moves toward a minus side at the next timing, and a case in which a coordinate moving toward the minus side with the lapse of time moves toward the plus side at the next timing. The relation detector 218 detects the number of times the moving direction is reversed along the X-axial direction and the number of times the moving direction is reversed along the Y-axial direction as the relation information.

The visual function detector 220 calculates a difference between the number of times the moving direction is reversed with respect to the X-axial direction and the number of times the moving direction is reversed with respect to the Y-axial direction as a difference number of times, and performs determination about whether the visual function of the test subject H satisfies the examination criterion based on this difference number of times. More specifically, the visual function detector 220 calculates a value obtained by subtracting the number of times the moving direction is reversed with respect to the Y-axial direction from the number of times the moving direction is reversed with respect to the X-axial direction as the difference number of times. The visual function detector 220 determines whether the difference number of times is larger than a threshold set in advance, determines that the visual function of the test subject H satisfies the examination criterion if the difference number of times is larger than the threshold, and determines that the visual function of the test subject H does not satisfy the criterion if the difference number of times is not larger than the threshold.

When the determination is thus performed based on the moving average, minute movements of the eyeball 111 (fixational eye movements) can be removed by the moving average as a low-pass filter, and appropriate determination can be performed. However, the determination by the visual function detector 220 is not limited to the one based on the difference moved distance or the moving average. The visual function detector 220 may detect the visual function of the test subject H based on a vector component along the moving direction of the image 231 for determination, the moving direction included in the moving direction of the gazing point 166, and on a vector component along a direction orthogonal to the moving direction. That is, the visual function detector 220 derives a determination result that there is a high possibility that the test subject H can visually recognize the image 231 for determination when the degree of the vector component along the moving direction of the image 231 for determination being larger than the vector component along the direction orthogonal to the moving direction is higher. However, the visual function detector 220 only needs to derive the determination result based on the moving direction of the gazing point 166 and the moving direction of the image 231 for determination, and may drive the determination result by another method.

Figure 18:
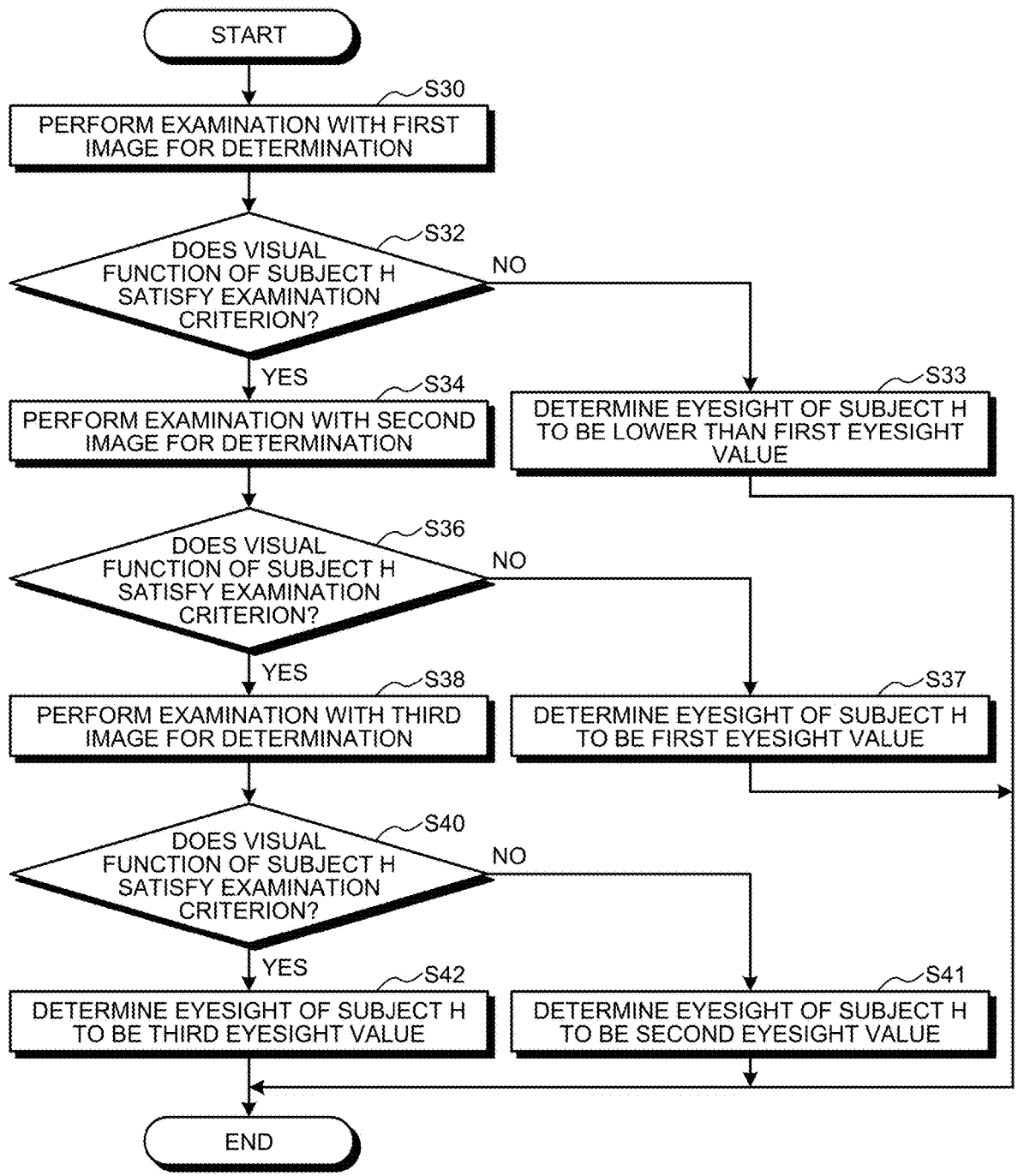
FIG. 18 is a flowchart of a method of detecting a visual function step by step.

The visual function detection apparatus 100 displays the image 231 for determination with different patterns to detect the degree of the visual function of the test subject H step by step. The following describes the method. FIG. 18 is a flowchart of a method of detecting a visual function step by step. FIG. 18 is the flowchart illustrating an exemplary case in which the eyesight of the test subject is detected. As illustrated in FIG. 18, the visual function detection apparatus 100 first performs an examination with a first image for determination (Step S30). The first image for determination is an image, in which the area of the first images 241 and the second images 242 is larger among the image 231 for determination with a plurality of patterns, and is the image 231A for determination illustrated in FIG. 10 in the example of the present embodiment. The visual function detection apparatus 100, at Step S30, executes the examination illustrated in FIG. 13 using this first image for determination (the image 231A for determination). That is, in this case, the visual function detection apparatus 100 displays the first image for determination (the image 231A for determination) to determine whether the visual function of the test subject H satisfies the examination criterion.

When determining that the visual function of the test subject H does not satisfy the examination criterion by the examination with the first image for determination (No at Step S32), the visual function detection apparatus 100 determines the eyesight of the test subject H to be lower than a first eyesight value (Step S33), and ends the present processing. The first eyesight value is an eyesight when it is determined that the visual function of the test subject H satisfies the examination criterion of the first image for determination, and is 0.3, for example. However, the value of the first eyesight value is set depending on the shape of the first image for determination, i.e., the size of the first images 241 and the second images 242.

When determining that the visual function of the test subject H satisfies the examination criterion by the examination with the first image for determination (Yes at Step S32), the visual function detection apparatus 100 performs an examination with a second image for determination (Step S34). The second image for determination is an image smaller in the area of the first images 241 and the second images 242 than the first image for determination, and is the image 231B for determination illustrated in FIG. 11 in the example of the present embodiment. The visual function detection apparatus 100, at Step S34, executes the examination illustrated in FIG. 13 using this second image for determination (the image 231B for determination) to determine whether the visual function of the test subject H satisfies the examination criterion.

When determining that the visual function of the test subject H does not satisfy the examination criterion by the examination with the second image for determination (No at Step S36), the visual function detection apparatus 100 determines the eyesight of the test subject H to be the first eyesight value (Step S37), and ends the present processing. When determining that the visual function of the test subject H satisfies the examination criterion by the examination with the second image for determination (Yes at Step S36), the visual function detection apparatus 100 performs an examination with a third image for determination (Step S38). The third image for determination is an image smaller in the area of the first images 241 and the second images 242 than the second image for determination, and is the image 231C for determination illustrated in FIG. 12 in the example of the present embodiment. The visual function detection apparatus 100, at Step S38, executes the examination illustrated in FIG. 13 using this third image for determination (the image 231C for determination) to determine whether the visual function of the test subject H satisfies the examination criterion.

When determining that the visual function of the test subject H does not satisfy the examination criterion by the examination with the third image for determination (No at Step S40), the visual function detection apparatus 100 determines the eyesight of the test subject H to be a second eyesight value (Step S41), and ends the present processing. The second eyesight value is an eyesight when it is determined that the visual function of the test subject H satisfies the examination criterion of the second image for determination, and is a value larger than the first eyesight value. The second eyesight value is 0.5, for example. However, the value of the second eyesight value is set depending on the shape of the second image for determination, i.e., the size of the first images 241 and the second images 242.

When determining that the visual function of the test subject H satisfies the examination criterion by the examination with the third image for determination (Yes at Step S40), the visual function detection apparatus 100 determines the eyesight of the test subject H to be a third eyesight value (Step S42), and ends the present processing. The third eyesight value is an eyesight when it is determined that the visual function of the test subject H satisfies the examination criterion of the third image for determination, and is a value larger than the second eyesight value. The third eyesight value is 1.0, for example. However, the value of the third eyesight value is set depending on the shape of the third image for determination, i.e., the size of the first images 241 and the second images 242. The visual function detector 220 derives information thus determined to be the eyesight values (the first eyesight value, the second eyesight value, and the third eyesight value) as information as a criterion for detecting eyesight as the visual function and stores the information in the storage unit 222, for example.

In the example in FIG. 18, upon the end of the examination with one image 231 for determination, the visual function detection apparatus 100 stops display of the image 231 for determination and starts the examination with the next image 231 for determination. However, the visual function detection apparatus 100 may continuously perform examinations with the images 231 for determination. In this case, upon a lapse of the detection time at Step S22 in FIG. 13, the visual function detection apparatus 100 may return to Step S12, display another image 231 for determination from the next frame, and perform an examination while scrolling the image 231 for determination within the display region 101T in a similar manner. The visual function detection apparatus 100 may display the image 231A for determination for a duration of the detection time, and then switch to the image 231B for determination, for example, to continue a similar examination from the next frame, for example. The examinations are thus continuously performed, whereby the detection time can be reduced. Further, the visual function detection apparatus 100 can also display the image 231B for determination for a duration of the detection time and then switch to the image 231A for determination, for example, from the next frame, or can return, when an image for a certain eyesight cannot be visually recognized, to an examination with an image for a lower eyesight than the image.

In the example in FIG. 18, when the visual function of the test subject H satisfies the examination criterion of the third image for determination, the eyesight value is determined to end the processing. However, when the image 231 for determination as a higher examination criterion is present, the processing may be continued. Examples of the image 231 for determination as a higher examination criterion include an image smaller in the size of the first images 241 and the second images 242 than the third image for determination. However, the image 231 for determination as a higher examination criterion may be the image 231 for determination smaller in contrast than the third image for determination.

Figure 19:
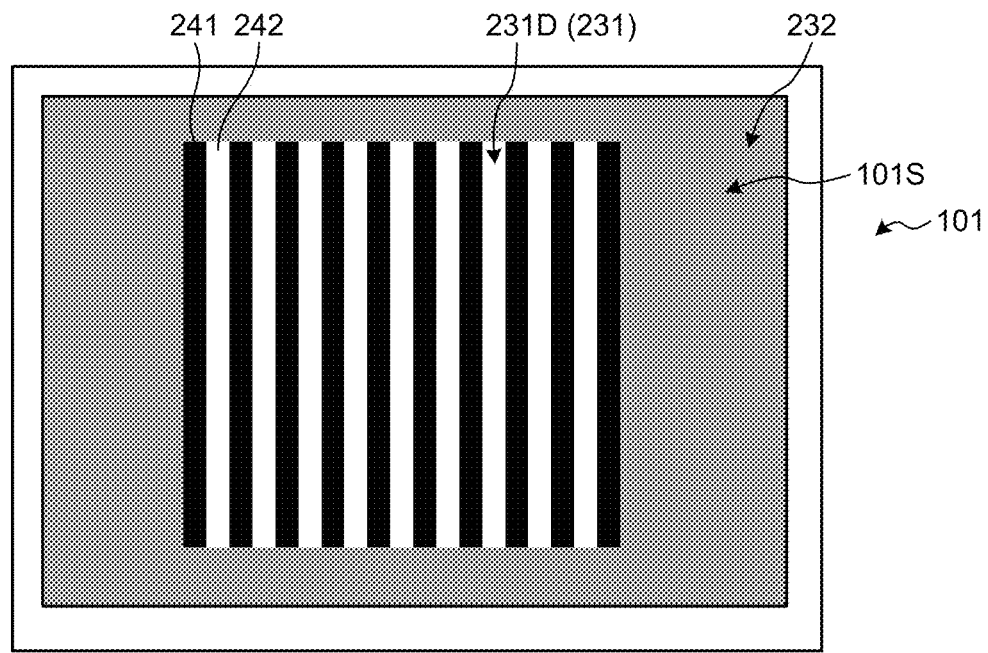
FIG. 19 is a diagram illustrating an example of the image for determination with a different contrast.
Figure 20:
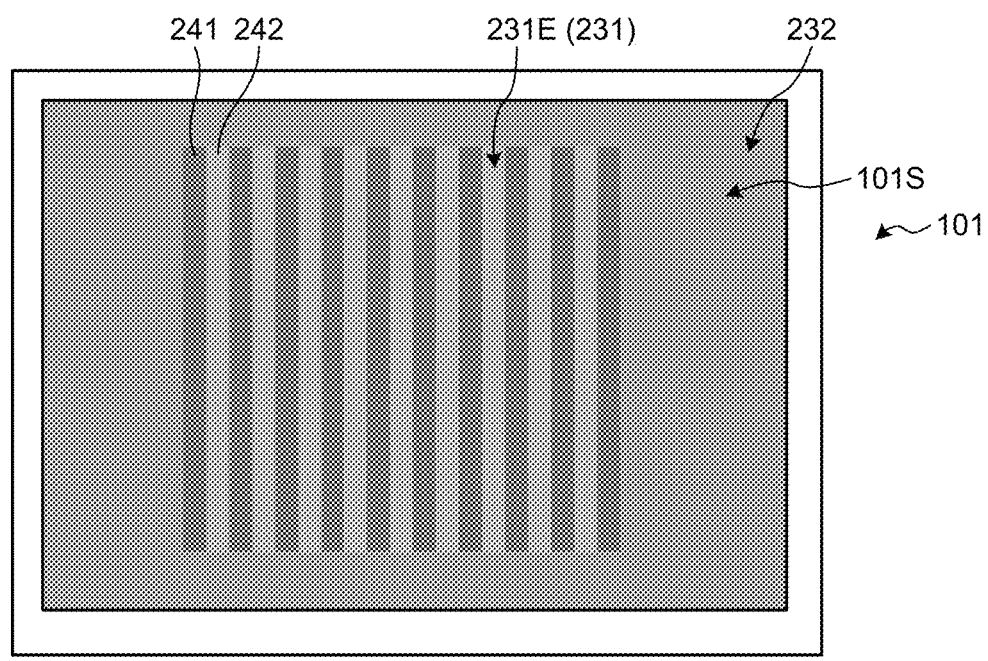
FIG. 20 is a diagram illustrating an example of the image for determination with a different contrast.

FIG. 19 and FIG. 20 are diagrams illustrating examples of the image for determination with different contrasts. The contrast referred to here is the degree of a luminance difference between maximum luminance and minimum luminance within the image 231 for determination. A larger degree of the luminance difference between the maximum luminance and the minimum luminance gives a larger contrast, whereas a smaller degree of the luminance difference between the maximum luminance and the minimum luminance gives a smaller contrast. The contrast is a value obtained by dividing the luminance of a pixel having maximum luminance among pixels within the image 231 for determination, i.e., the maximum luminance by the luminance of a pixel having minimum luminance among the pixels within the image 231 for determination, i.e., the minimum luminance, for example.

An image 231D for determination illustrated in FIG. 19 and an image 231E for determination illustrated in FIG. 20 are equal to each other in the size of the first images 241 and the second images 242. However, the image 231E for determination illustrated in FIG. 20 is smaller in contrast than the image 231D for determination illustrated in FIG. 19. That is, the image 231E for determination is smaller in the degree of the luminance difference between the maximum luminance and the minimum luminance than the image 231D for determination. Consequently, the image 231E for determination is more difficult for the test subject H to visually recognize than the image 231D for determination. In the present embodiment, the second images 242 have the maximum luminance, whereas the first images 241 have the minimum luminance. A smaller contrast gives a smaller luminance difference between the first images 241 and the second images 242, thus making it difficult for the test subject to visually recognize the image 231 for determination.

Thus, step-by-step examinations can be performed also by varying the contrast of the image 231 for determination. The visual function detection apparatus 100 may perform an examination using only the image 231 for determination varied in the size of the first images 241 and the second images 242, may perform an examination using only the image 231 for determination varied in contrast, or may use both of them or combine them with each other.

As described above, the visual function detection apparatus 100 according to the present embodiment includes the display controller 216, the gazing point detector 214, the relation detector 218, and the visual function detector 220. The display controller 216 displays the image 231 for determination on the display region 101T on the display screen 101S of the display unit (the display apparatus 101) and moves the image 231 for determination within the display region 101T. The gazing point detector 214 detects the position of the gazing point of the test subject H observing the display screen 101S on the display screen 101S. The relation detector 218 detects the relation information between the moving direction of the image 231 for determination and the moving direction of the gazing point 166. The visual function detector 220 detects the visual function of the test subject H based on the relation information. The visual function detection apparatus 100 displays the image 231 for determination attracting the attention of the test subject H to guide the line of sight of the test subject H to the image 231 for determination when the test subject H can visually recognize the image 231 for determination. Further, the visual function detection apparatus 100 displays the image 231 for determination such that the image 231 for determination moves within the display region 101T. Consequently, when the test subject H can visually recognize the image 231 for determination, the line of sight of the test subject H moves in a direction along the moving direction of the image 231 for determination more significantly. The visual function detection apparatus 100 detects the line of sight of the test subject as the gazing point and, based on the moving direction of the gazing point, determines whether the test subject H can visually recognize the image 231 for determination to detect the visual function of the test subject H. Consequently, the visual function detection apparatus 100 eliminates a declaration about whether the test subject H can visually recognize the image 231 for determination, can appropriately detect the gazing point, and can appropriately determine whether the test subject H can visually recognize the image 231 for determination based on the gazing point. Consequently, the visual function detection apparatus 100 can appropriately examine the visual function of the test subject H.

In the present embodiment, detection of the visual function is performed based on the moving direction of the gazing point 166. However, the visual function detection apparatus 100 may detect the visual function based on a direction in which the eyeball 111 of the test subject H moves without detecting the gazing point 166. That is, the visual function detection apparatus 100 may include: the display controller 216; a detector that detects movement of the eyeball 111 of the test subject H observing the display screen 101S; the relation detector 218 that detects relation information between the moving direction of the image 231 for determination and the moving direction of the eyeball 111; and the visual function detector 220 that detects the visual function of the test subject H based on the relation information. When the test subject H can visually recognize the image 231 for determination, the eyeball 111 moves in a direction along the moving direction of the image 231 for determination more significantly. Consequently, if a movement amount of the eyeball 111 or the number of times the eyeball 111 moves is larger in the moving direction than that in a direction orthogonal to the moving direction, the visual function detector 220 can derive information as a criterion of determination that the test subject H can visually recognize the image 231 for determination like the time of detection of the gazing point 166. The detector detects the movement of the eyeball 111 based on the image data of the eyeball 111 acquired by the image data acquisition unit 206. The detector may be the position detector 210, for example. In this case, the relation detector 218 can detect the relation information by a method similar to that of the gazing point 166 using the position data of the iris center detected by the position detector 210. The detector only needs to detect the movement of the eyeball 111 based on the image data of the eyeball 111, and is not limited to the position detector 210.

The display controller 216 displays the image 231 for determination on the entire region of the display region 101T, and the image 231 for determination includes the first images 241 and the second images 242 different from each other in luminance. The visual function detection apparatus 100 displays the image 231 for determination on the entire region of the display region 101T, and further displays the first images 241 and the second images 242 different from each other in luminance as the image 231 for determination. Accordingly, the visual function detection apparatus 100 can appropriately guide the line of sight and appropriately examine the visual function when the test subject H can visually recognize the image 231 for determination.

The display controller 216 scrolls the first images 241 and the second images 242 in a certain direction within the display region 101T. The visual function detection apparatus 100 scrolls the first images 241 and the second images 242 and can thereby, when the test subject H can visually recognize the image 231 for determination, appropriately guide the line of sight and appropriately examine the visual function.

The display controller 216 displays the first images 241 and the second images 242 within the display region 101T. The display controller 216 displays the first images 241 and the second images 242 at the end of the display region 101T opposite to the certain direction (the X-axial direction in the present embodiment) so as to gradually increase in area and, when the first images 241 and the second images 242 reach a certain area, moves the first images 241 and the second images 242 in the certain direction. The visual function detection apparatus 100 thus scrolls the first images 241 and the second images 242 and can thereby, when the test subject H can visually recognize the image 231 for determination, appropriately guide the line of sight and appropriately examine the visual function.

When the first images 241 and the second images 242 move to the end of the display region 101T in the certain direction (the X-axial direction in the present embodiment), the display controller 216 gradually reduces the first images 241 and the second images 242 in area and then ends display of the first images 241 and the second images 242 at the end in the certain direction. The visual function detection apparatus 100 thus scrolls the first images 241 and the second images 242 and can thereby, when the test subject H can visually recognize the image 231 for determination, appropriately guide the line of sight and appropriately examine the visual function.

The display controller 216 displays the first images 241 and the second images 242 within the display region 101T and displays a plurality of types of the images 231 for determination different from each other in the size of the first images 241 and the second images 242 at different times. The visual function detector 220 detects the visual function of the test subject H based on relation information for each of the types of the images 231 for determination. The visual function detection apparatus 100 performs an examination for each of the types of the images 231 for determination and can thereby evaluate the visual function step by step.

The display controller 216 displays a plurality of types of the images 231 for determination different from each other in contrast at different times, and the visual function detector 220 detects the visual function of the test subject H based on relation information for each of the types of the images 231 for determination. The visual function detection apparatus 100 performs an examination for each of the types of the images 231 for determination different from each other in contrast and can thus evaluate the visual function step by step.

The visual function detector 220 detects the visual function of the test subject H based on the vector component along any direction (the first direction) included in the moving direction of the gazing point 166 and on the vector component along the direction orthogonal to the first direction The visual function detector 220 resolves the moving direction of the gazing point 166 into the vector component along the moving direction of the image 231 for determination and the vector component along the direction orthogonal to the moving direction to perform evaluation. Consequently, the visual function detection apparatus 100 appropriately detects the movement of the gazing point 166 along the moving direction of the image 231 for determination and can thereby appropriately evaluate the visual function.

Figure 21:
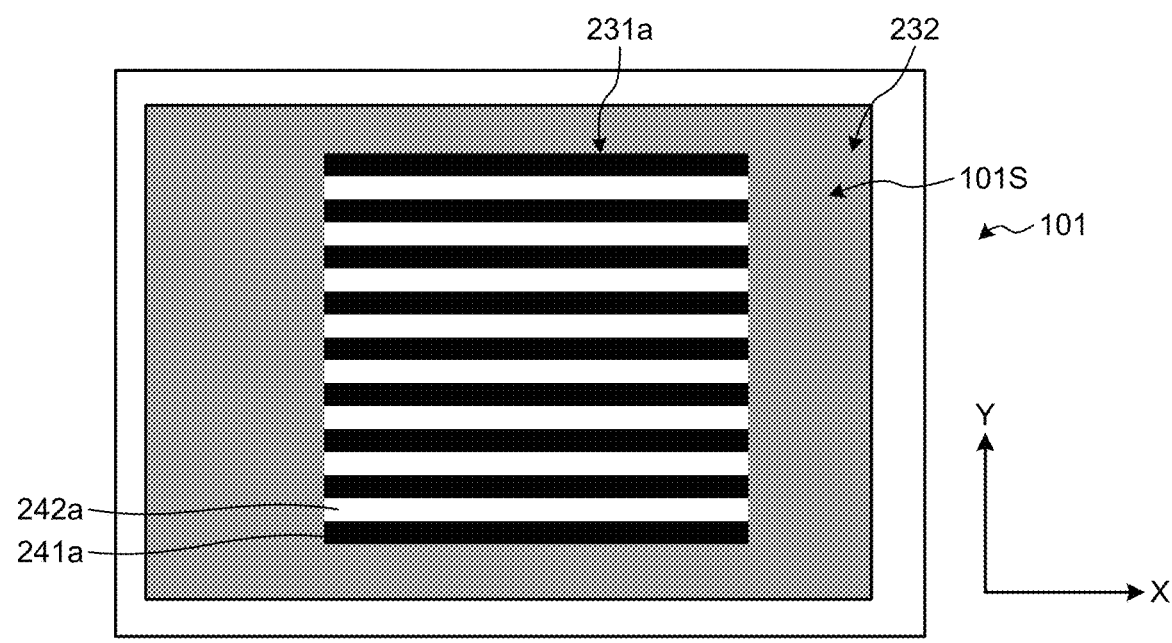
FIG. 21 is a diagram illustrating another example of the image for determination.
Figure 22:
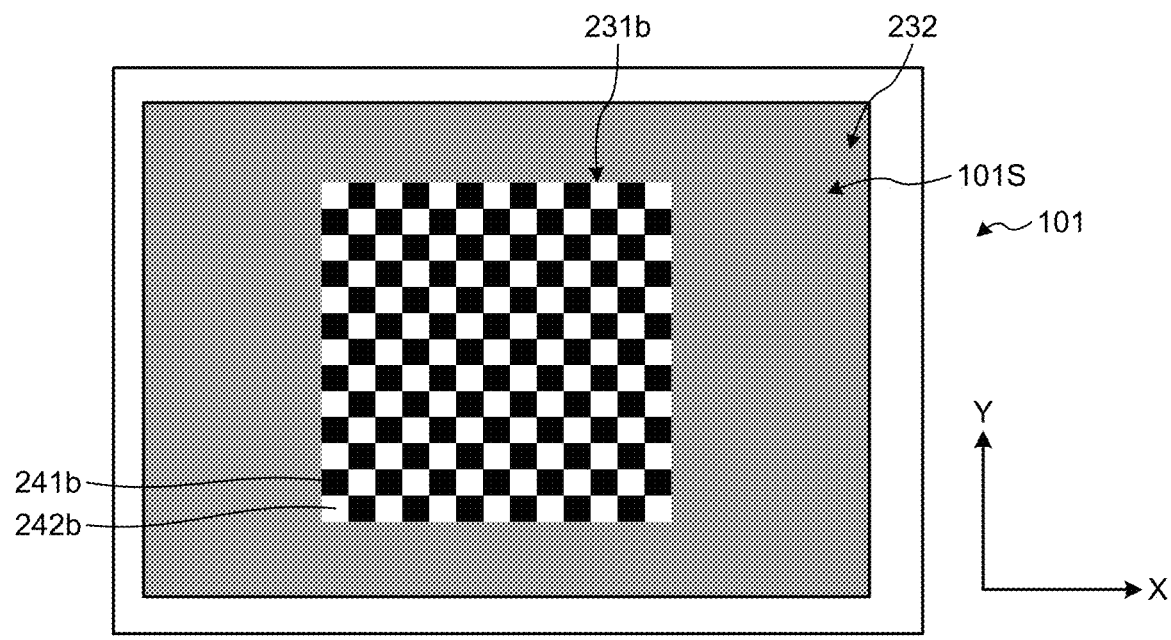
FIG. 22 is a diagram illustrating another example of the image for determination.
Figure 23:
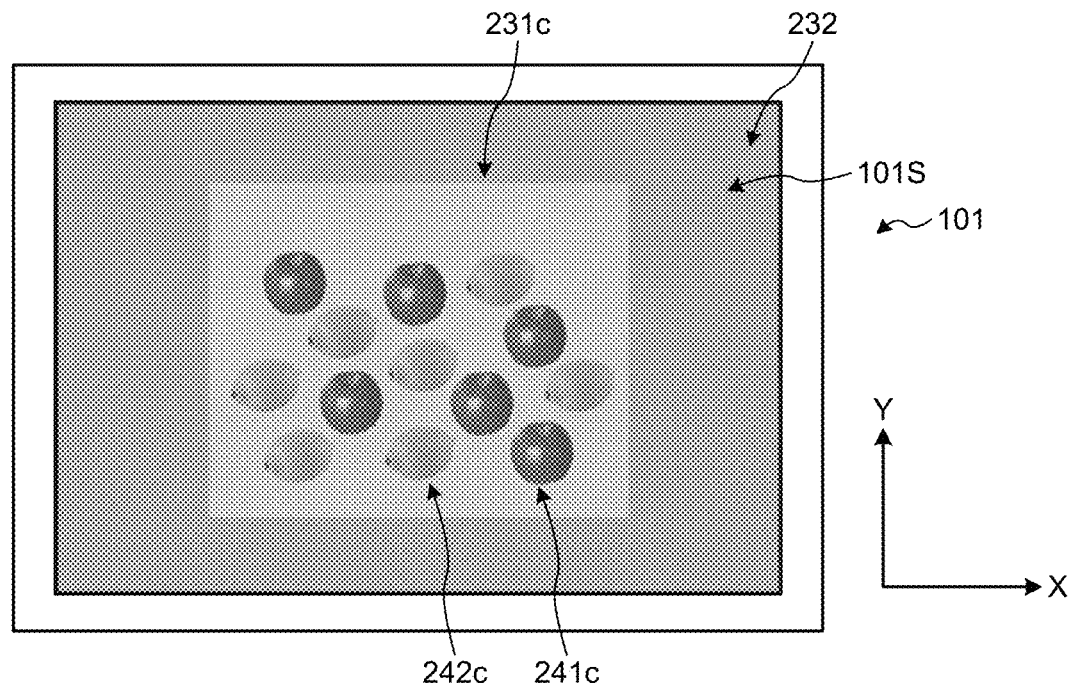
FIG. 23 is a diagram illustrating another example of the image for determination.

FIG. 21 to FIG. 23 are diagrams each illustrating another example of the image for determination. While the image 231 for determination of the present embodiment has a stripe shape in which the first images 241 and the second images 242 are alternately arranged along the X-axial direction, display of the image 231 for determination is not limited to this example. As illustrated in an image 231a for determination in FIG. 21, for example, the image 231 for determination may have a stripe shape in which first images 241a and second images 242a are alternately arranged along the Y-axial direction. In this case, the moving direction of the image 231 for determination is preferably the Y-axial direction. The visual function detection apparatus 100 performs an examination while switching between the image 231 for determination and the image 231a for determination, and can thereby detect both a reaction to movement in the X-axial direction and a reaction to movement in the Y-axial direction. The movement direction of the image 231 for determination is not limited to the X-axial direction and the Y-axial direction and may be a direction crossing both the X-axial direction and the Y-axial direction, i.e., an oblique direction, for example.

As illustrated in an image 231b for determination in FIG. 22, the image 231 for determination may have a checkered pattern in which first images 241b and second images 242b are alternately arranged along the X-axial direction and the Y-axial direction. As illustrated in an image 231c for determination in FIG. 23, first images 241c and second images 242c may be images different from each other in luminance and shape. While in the example in FIG. 23, the first images 241c and the second images 242c are fruits, the images are not limited to fruits.

While the embodiments of the present invention have been described, the details of these embodiments do not limit the embodiments. The components described above include ones that those skilled in the art can easily think of, substantially the same ones, and ones within what is called equivalents. Further, the components described above can be combined with each other as appropriate. Further, various omissions, replacements, or modifications of the components can be made within the scope not departing from the gist of the embodiments described above.

What is claimed is:

1. A vision function detection apparatus comprising:
a display controller configured to cause an image for determination to be displayed in a display region on a display screen of a display unit, and move the image for determination within the display region;
a gazing point detector configured to detect a position of a gazing point of a test subject observing the display screen;
a relation detector configured to detect relation information between movement of the gazing point in a first direction along a moving direction of the image for determination and movement of the gazing point in a second direction orthogonal to the first direction; and
a visual function detector configured to detect a visual function of the test subject based on the relation information, wherein
the visual function detector is configured to detect the visual function of the test subject based on:
a first difference between a first total moved distance of the gazing point in the first direction along the moving direction of the image for determination and a second total moved distance of the gazing point in the second direction orthogonal to the first direction; or
a second difference between a first number of times a moving direction of the gazing point is reversed with respect to the first direction along the moving direction of the image for determination and a second number of times the moving direction of the gazing point is reversed with respect to the second direction orthogonal to the first direction.

2. A vision function detection apparatus comprising:
a display controller configured to cause an image for determination to be displayed in a display region on a display screen of a display unit, and move the image for determination within the display region;
a detector configured to detect movement of an eyeball of a test subject observing the display screen;
a relation detector configured to detect relation information between movement of the eyeball in a first direction along a moving direction of the image for determination and movement of the eyeball in a second direction orthogonal to the first direction; and
a visual function detector configured to detect a visual function of the test subject based on the relation information, wherein
the visual function detector is configured to detect the visual function of the test subject based on:
a first difference between a first total moved distance of the eyeball in the first direction along the moving direction of the image for determination and a second total moved distance of the eyeball in the second direction orthogonal to the first direction; or a second difference between a first number of times a moving direction of the eyeball is reversed with respect to the first direction along the moving direction of the image for determination and a second number of times the moving direction of the eyeball is reversed with respect to the second direction orthogonal to the first direction.

3. A method of detecting a vision function, the method comprising:
performing display control to cause an image for determination to be displayed in a display region on a display screen of a display unit and moving the image for determination within the display region;
performing gazing point detection to detect a position of a gazing point of a test subject observing the display screen;
performing relation information detection to detect relation information between movement of the gazing point in a first direction along a moving direction of the image for determination and movement of the gazing point in a second direction orthogonal to the first direction; and performing visual function detection to detect a visual function of the test subject based on the relation information, wherein
the performing of the visual function detection detects the visual function of the test subject based on:
a first difference between a first total moved distance of the gazing point in the first direction along the moving direction of the image for determination and a second total moved distance of the gazing point in the second direction orthogonal to the first direction; or
a second difference between a first number of times a moving direction of the gazing point is reversed with respect to the first direction along the moving direction of the image for determination and a second number of times the moving direction of the gazing point is reversed with respect to the second direction orthogonal to the first direction.

* * * * *